United States Patent [19]
Helentjaris et al.

[11] Patent Number: 5,385,835
[45] Date of Patent: Jan. 31, 1995

[54] IDENTIFICATION AND LOCALIZATION AND INTROGRESSION INTO PLANTS OF DESIRED MULTIGENIC TRAITS

[75] Inventors: Timothy Helentjaris; James Nienhuis, both of Salt Lake City, Utah

[73] Assignee: Pioneer Hi-Bred International, Inc., Des Moines, Iowa

[21] Appl. No.: 252,371

[22] Filed: May 19, 1994

Related U.S. Application Data

[63] Continuation of Ser. No. 94,621, Jul. 20, 1993, which is a continuation of Ser. No. 747,496, Aug. 19, 1991, which is a continuation of Ser. No. 534,196, Jun. 5, 1990, abandoned, which is a continuation of Ser. No. 81,989, Aug. 4, 1987.

[51] Int. Cl.$^6$ .................... C12N 15/01; A01H 1/00
[52] U.S. Cl. .................... 435/172.3; 435/6; 47/58; 47/DIG. 1
[58] Field of Search ........... 435/172.1, 172.2, 172.3, 435/6; 47/58.03, 58.05; 935/6, 91; 536/23.1, 24.3

[56] References Cited

FOREIGN PATENT DOCUMENTS 0242991 10/1987 European Pat. Off. .

OTHER PUBLICATIONS

Burr et al. (1983) in *Genetic Engineering Principles and Methods* 0015, pp. 45–59 "The Application of Restruction Fragment Length Polymophisin to Plant Breeding".
Soller et al. (1983) *Theoretical and Applied Genetics* vol. 67, pp. 25–33 "Genetic polymorphisin in varietid identification & genetic imporovement".
*Webster II New Riverside University Dictionary*, p. 1155.
Rowe et al. (1984), *Can. J. Plant Sci.* 64:145–150 Indirect Selection for Resistance to Sclerotina Crown and Stem Rot on Alfalfa.
Hartl; D. L. (1980) *Principles of Population Genetics* p. 18, Sinauer Associates Inc. Sunderland Mass.
Allard, R. W. (1980), *Principles of Plant Breeding* p. 85 John Wiley & Sons Inc. New York, N.Y.
Sox (1923) *Genetics*, 8, pp. 552–560.
Tanksley, (1983) *Plant Molecular Biology Reporter*, vol. #1 pp. 3–8.
Tonksley et al. (1982), *Heredity* vol. 49(1) pp. 11–25.
Nienhuis et al. "Restriction fragment length polymorphism analysis of loci associated with insect resistance in tomato", *Crop Science*, 27(4):797:803 (1987).
Nienhuis et al. "Restriction fragment length mapping of loci associated with insect resistance in tomato", Abstract No. 881669880, *Commonwealth Agricultural Bureau*, (Meeting held May 29–30, 1986).
Helentjaris et al. "Construction of genetic linkage maps in maize and tomato using restriction fragment length polymorphisms", *Theor. Appl. Genet.*, 72:761–769 (1986).
Helentjaris et al. "Restriction fragment polymorphisms as probes for plant diversity and their development as tools for applied plant breeding", *Plant Mol. Biol.*, 5:109–118 (1985).
Ellis "Restriction fragment length polymorphism markers in relation to quantitative characters", *Theor. Appl. Genet.*, 72:1–2 (1986).
Michelmore & Shaw "Character dissection", *Nature*, 335: 672–673 (1988).

(List continued on next page.)

Primary Examiner—Gary Benzion
Attorney, Agent, or Firm—Foley and Lardner

[57] ABSTRACT

Methods of introgressing one or more desired quantitative traits into a plant comprising screening one or more restriction fragment length polymorphisms (RFLP) for association with desired quantitative traits (QT), selecting one or more RFLP's showing association with the desired QT's, developing a mathematical model based on the magnitude of the association of RFLP(s) to predict the degree of expression of the desired QT's, and using the thus-selected RFLP(s) and the mathematical model in a plant breeding program to predict the degree of introgression and expression of the desired QT's in plant progeny.

7 Claims, 15 Drawing Sheets

OTHER PUBLICATIONS

Evola et al. "The suitability of restriction fragment length polymorphisms as genetic markers in maize", *Theor. Appl. Genet.*, 71:765–771 (1986).

Stuber et al. "Molecular marker-facilitated investigations of quantitative trait loci in Maize. II Factors influencing yield and its component traits", *Crop Sci.*, 27:639–648 (1987).

Soller et al. "The expected distribution of marker-linked quantitative effects in crosses between inbred lines", Heredity, 43(2): 179–190 (1979).

Soller & Genizi "The efficiency of experimental designs for the detection of linkage between a marker locus and a locus effecting a quantitative trait in segregating populations", *Biometrics*, 34: 47–55 (1978).

Soller & Plotkin-Hazan "The use of marker alleles for the introgression of linked quantitative alleles", *Theor. Appl. Genet.* 51: 133–137 (1977).

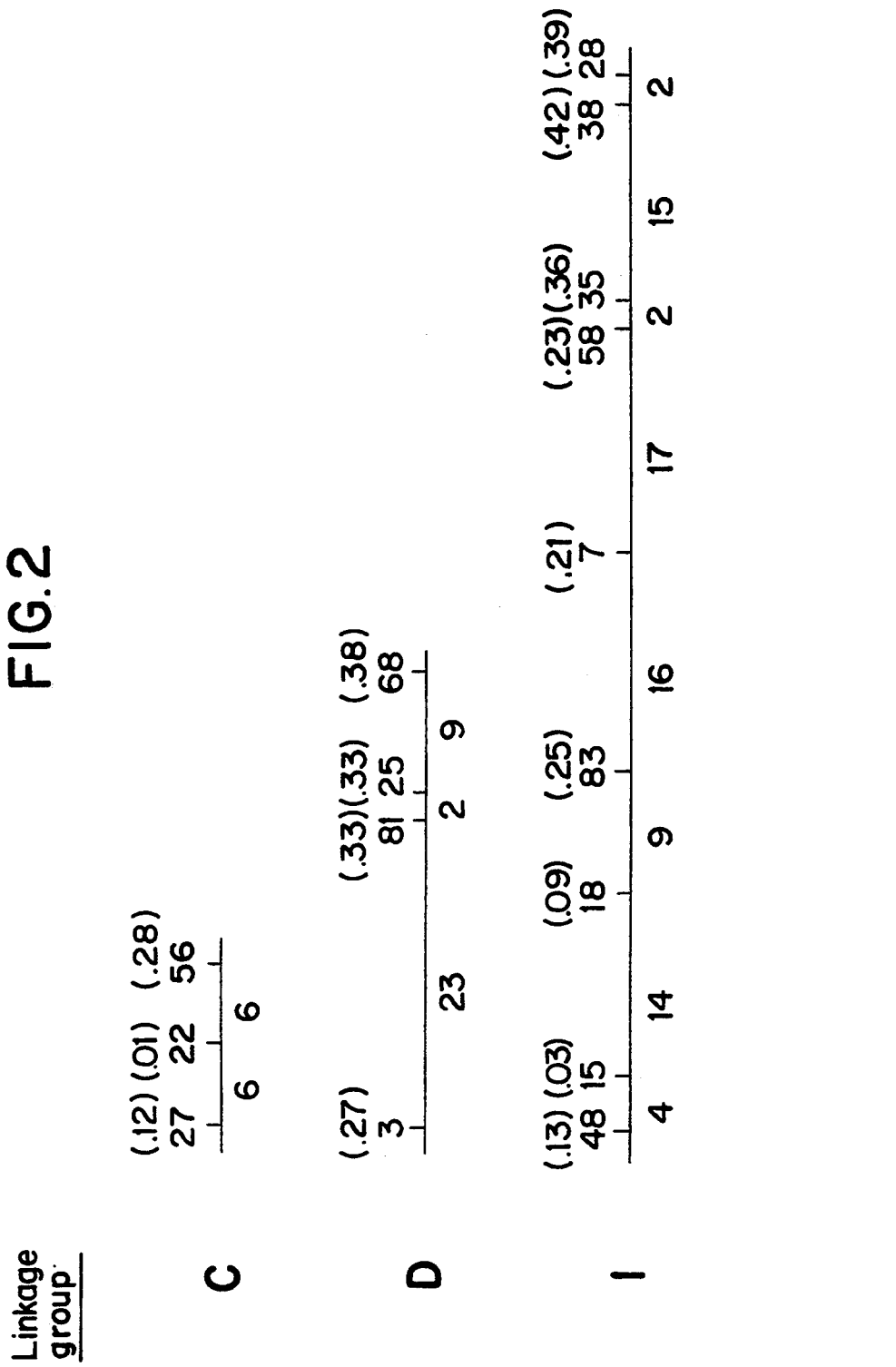

Observed colorimetric absorbance values (2TD).

FIG. 6
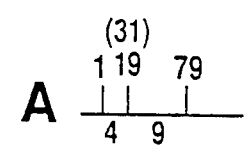
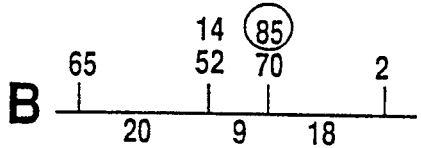
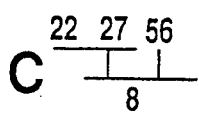
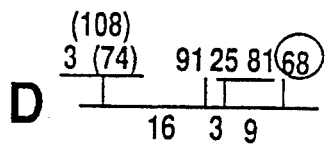
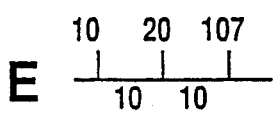
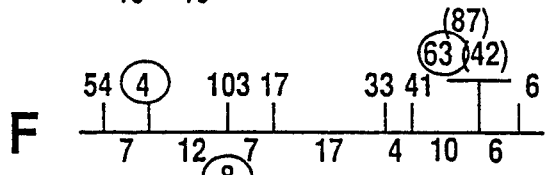
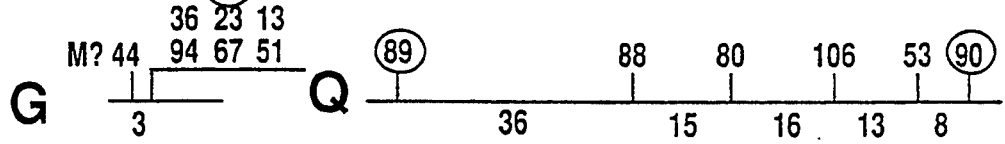
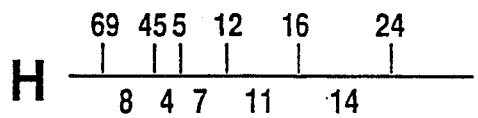
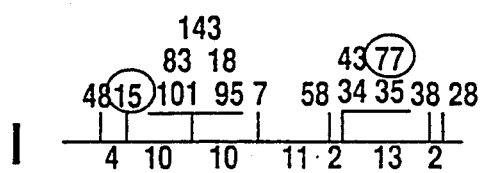
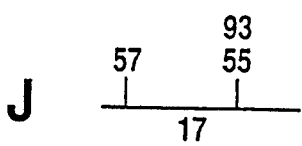
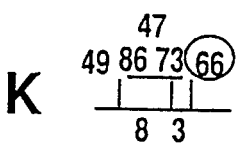
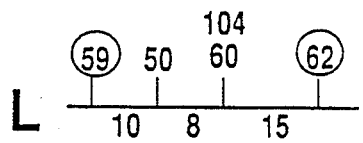
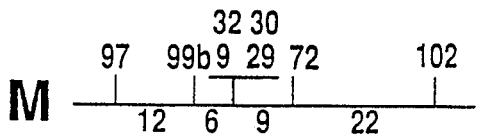
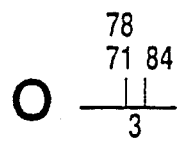
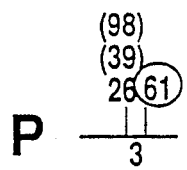
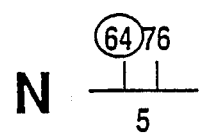
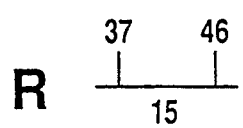
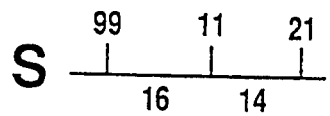
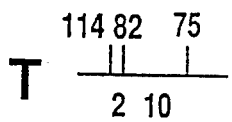

Unlinked Clones 40 96 105 109 119 118

Unlinked Clones 40 96 105 109 119 118

Unlinked Clones 40 96 105 109 119 118

IDENTIFICATION AND LOCALIZATION AND INTROGRESSION INTO PLANTS OF DESIRED MULTIGENIC TRAITS

This is a continuation application of prior application Ser. No. 08/094,621, filed on Jul. 20, 1993, which is a continuation of Ser. No. 07/747,496, filed Aug. 19, 1991, which was a continuation of Ser. No. 534,196 filed Jun. 5, 1990, now abandoned, which was a continuation of Ser. No. 07/081,989, filed Aug. 4, 1987.

BACKGROUND

FIELD OF THE INVENTION

The field of the invention is plant genetics, including genetic mapping and restriction fragment length polymorphism technology.

DESCRIPTION OF RELATED ART AND INTRODUCTION TO THE INVENTION

When considering the application of biotechnology to plant improvement, a great deal of emphasis is usually placed on the strategy of introducing novel variability into plants via genetic engineering techniques. Over the past decade, advances have been made in developing methods of transferring genes to plant cells (see Potrykus et al., Plant Mol. Bio. Rep. 3:117-128 (1985)). For example, transfer and expression of single genes improving insect and herbicide resistance has reportedly been achieved in plants (Abel et al., Science 232:738-743 (1986); Shah et al., Science 233:478-481 (1986)). While there is excitement over advances in plant genetic engineering, the prospects for the general use of these techniques for plant improvement are tempered by the realization that very few genes corresponding to plant traits of interest have been identified or cloned.

One procedure that has been used by plant breeders to increase efficiency in the testing of traits which are difficult or expensive to evaluate is the use of indirect selection criteria (Hallaver and Miranda, Quantitative Genetics in Corn Breeding (Iowa State University Press 1981). One indirect selection criterion, for example, might be an easily recognized morphological characteristic of the plant which is either genetically linked to the desired trait or perhaps a component of the desired trait, e.g., the association between leaf size and seed size in beans.

Agronomically important traits such as, for example, plant yield, height, maturity, and fruit and grain characteristics, are all attractive targets for manipulation in plant improvement programs, but often have very low heritabilities. Heritability is the ratio of genetic to total variation and, therefore, is important to the efficiency of the selection process. Influencing heritability of such traits, sometimes termed "quantitative" traits, is difficult, however, because expression of a number of different gene products generally influences the phenotype. Quantitative traits are characterized by continuous rather than discreet distribution of phenotypic expression. There is currently a poor understanding of how single genes influence the expression of complex traits and, in conventional plant breeding programs, selection for inheritance of quantitative traits is difficult due to the unrecognized genetic basis of the trait. The use of direct gene transfer in manipulating these traits, of course, is therefore difficult due to problems in pinpointing and then cloning those individual loci which contribute predominantly to the expression of the trait. Determination of genotypic information from phenotypic values is further imprecise because evaluation of the trait may frequently be confounded by environmental effects (Berger, "Multiple-Trait Selection Experiments: Current Status, Problem Areas and Experimental Approaches." In: Proceedings of the International Conference on Quantitative Genetics (Pollack et al., Eds.), p. 191-204 (Iowa St. Press 1977)).

Clearly, one area in which biotechnology may have a significant impact on plant improvement is in the development of new methods to identify and characterize the role of individual plant genes in quantitative trait expression. Following the development of a new class of plant molecular markers based on restriction fragment length polymorphisms, termed "RFLPs", (Helentjaris et al., Plant Mol. Bio. 5:109-118 (1985)) ("Helentjaris et al. I"), the processes to identify such loci and discriminate gene effects have been invented and are described and claimed herein. This and all other publications noted herein are hereby incorporated by reference. This will undoubtedly benefit plant improvement, not only within the context of conventional breeding approaches, but also by providing a means for identifying appropriate loci for future cloning and direct gene transfer efforts.

RFLPs are differences observed between genotypes in the fragment lengths of restriction endonuclease-digested DNA. RFLPs occur as a result of base pair or positional changes in the restriction enzyme recognition sites which flank a chromosomal location and can be detected by hybridization of labelled DNA clones containing sequences that are homologous to a portion of the chromosomal fragment. Hybridization with a unique cloned sequence can permit the identification of a specific chromosomal region (locus).

This technology employs cloned DNA fragments to detect differences between individuals at the DNA sequence level. When genomic DNAs from two genetically distinct individuals are digested with a restriction enzyme, electrophoresed and probed with a labelled DNA clone, polymorphisms in the hybridization patterns sometimes result due to sequence differences between the individuals. The term "restriction fragment length polymorphism" has been coined to describe this variation.

Differences in fragment lengths which are revealed, for example, by agarose gel electophoresis, function as alleles of that RFLP. Thus, RFLPs can serve as genetic markers in a manner analogous to conventional morphological or isozyme markers. Unlike most genetic markers, however, they are not the products of transcription and translation. Additionally, RFLP possess certain additional advantages over previously available genetic markers. First, RFLPs reflect existing differences between genetically distinct individuals. The potential number of RFLPs for all practical purposes is thus unlimited, as digestion of the genomic DNA of any higher eukaryote with a six base recognition enzyme will generate more than a million fragments, many of which can be polymorphic. Additionally, over one hundred different restriction enzymes have now been described, each of which may generate a new and different set of fragments (Roberts, Nuc. Acids Res. 10:117-144 (1982)). The utility of isozyme markers or morphological markers in studies is frequently limited by a lack of informativeness in lines of interest or by an insufficient availability or chromosomal distribution of the loci.

The use of isozyme variation in plant breeding is, like RFLP technology, one of indirect selection. (Tanskley and Orton, *Isozymes in Plant Genetics and Breeding* 1B (Elsevier, N.Y. 1983). The time required to backcross a trait from a donor to a recurrent parent is the product of the generation time by the number of generations. Therefore, screening for traits linked to isozymes, which may sometimes be identified in seeds or seedlings, can reduce the time required for evaluation, especially if the expression of that trait is controlled by recessive alleles. In addition, the number of backcross generations necessary to sufficiently recover the phenotype of the recurrent parent can be reduced by selection for isozymes associated with the recurrent parent.

In tomato, closely linked isozyme variation has been used to follow the inheritance of several simply inherited traits such as, for example, nematode resistance (Rick and Fobes, *Rep. Tomato Genet. Coop.* 24:25 (1974)). The inheritance of quantitative traits has also been followed by the use of multiple isozyme loci. For example, in tomato, eleven isozyme loci were used to survey eight of the 12 chromosomes and three independent genetic factors were detected in association with cold tolerance (Vallejos and Tanksley, *Theor. Appl. Genet.* 66:241-247 (1983)). In maize, changes in the frequency of eight isozyme loci were found to be associated with selection for improved grain yield (Stuber et al., *Crop. Sci.* 22:737-740 (1982)). Nevertheless, for a multigenic trait, only that portion of the genome closely linked to an isozyme marker can be considered, and many other major or minor genes may be associated with the expression of quantitative traits.

Maize is perhaps the best characterized plant system in terms of isozymes and yet only about two dozen isozyme loci have been located and it is rare for more than a dozen of these to be informative in any particular cross involving Corn Belt germplasm. By contrast, using the inventors' RFLP technology, over 300 RFLPs covering all ten maize chromosomes have been characterized (Helentjaris et al., *Trends in Genetics.* 3:217-221 (1987)). The level of informativeness of these RFLPs is great. In a study involving the maize cross Tx303×Co159, only 13 informative isozyme loci with very biased coverage of less than the 10 chromosomes were available. In contrast, using RFLP analysis, more than 99 informative RFLPs covering all 10 chromosomes can be analyzed in the same cross (unpublished data). In a recent comparative survey of Corn Belt germplasm RFLPs averaged greater than five alleles per locus while isozyme loci averaged less than two (M. Walton and T. Helentjaris, abstract).

RFLP markers rarely possess detectable phenotype effects of their own, so they can be utilized in economic lines without detriment and many can be evaluated at one time without the pleiotropic effects often seen with phenotypic markers. Evaluation can be performed on small amounts of DNA obtained from plant tissue at virtually any stage of plant development from roots, to shoots, to fruits, or even with tissue culture material. Evaluation of RFLPs is not affected by environmental factors and greenhouse-grown plants will not differ from field-grown plants when tested. Finally, the evaluation of RFLPs reveals the exact genotype, so the heterozygous state can be differentiated from the homozygous condition at any chromosomal location.

Many of the potential applications and theoretical advantages of RFLPs compared to more conventional phenotypic or isozyme marking systems have been described previously. Helentjaris et al. I. In one application of the use of RFLP markers in plant studies, genetic linkage maps based on these markers have been constructed for both maize and tomato (Helentjaris et al., *Theor. Appl. Genet.* 72:761-769 (1986)) ("Helentjaris et al. II"). Similar linkage maps are also being constructed for other crop species, such as Brassica Figdore et al., *Theor. Appl. Genetics.* 75:833-840 (1988); Slocum et al., In "Genetic Maps" (S. J. O'Brien, ed.), 5th Edition, Cold Spring Harbor Press, N.Y. (1990)). Close to 120 RFLPs in tomato have been arranged into linkage groups by comparing segregation patterns in an F2 population derived from homozygous parental lines. Approximately 70 RFLPs have been mapped by another group of workers. Bernatzky and Tanksley, *Genetics* 112:887-898 (1986). Over 300 RFLPs in maize have been arranged into linkage groups (Helentjaris et al., 1986; Helentjaris et al., 1987). The locations of the maize RFLP loci have been correlated to the conventional maize genetic map by analyzing the inheritance patterns of the RFLPs in maize lines monosomic for different chromosomes (Helentjaris et al., *Proc. Nat. Acad. Sci. USA* 83:6035-6039 (1986)) ("Helentjaris et al. III"), by establishing linkage relationships with isozyme markers, cloned genes, and morphological markers with previously identified chromosomal locations (Wright et al., MNL 61:89-90 (1987)), and by analyzing inheritance patterns in B-A translocation stocks (Helentjaris et al., Weber and Helentjaris, Genetics 121:583-590 (1989). The resulting map (FIG. 1) shows the resolution possible.

Numerous direct applications of RFLP technology to facilitate plant breeding programs have been suggested. Helentjaris et al. I. Because of the large numbers of RFLP markers available in a population of interest, one of the more important applications of RFLPs may be as markers linked to genes affecting the expression of quantitatively inherited traits. In this application, RFLPs function as indirect selection criteria for traits which are difficult or expensive to evaluate phenotypically. A prerequisite for the use of RFLPs as indirect selection criteria is the identification of RFLPs closely linked to the quantitative trait loci (QTL) affecting expression of the trait of interest.

Currently, the introgression of quantitative traits from one germplasm to another involves the identification of favorable genotypes in segregating generations followed by repeated backcrossing to commercially acceptable cultivars. This procedure is feasible for simply inherited quantitative traits, but as the number of genes controlling a trait increases, screening the number of F2 segregants required to identify at least one individual which represents the ideal (homozygous) genotype quickly becomes prohibitive. For example, with one gene and two alleles of equal frequency, the probability of recovering a desirable genotype in the F2 generation is $\frac{1}{4}$. However, if the number of genes is increased to 5 or 10, the probability of recovering an ideal genotype in the F2 population is reduced to approximately one in one thousand and one in one million, respectively. Thus, to identify desirable segregants, one must either reduce the number of segregants needed or have available very efficient screening procedures. Additionally, in situations where enviromental effects interfere with the ability to draw accurate genotypic information from the phenotype, large allocations of time and resources are required to evaluate progeny in replicated trials within several target environments.

Described and claimed herein is the use of RFLPs to dissect multigenic traits into their individual genetic components. A genome, or portion thereof, saturated with RFLPs or probed with select RFLP markers, all of which can be evaluated together in individual plants, has been found to give the resolution necessary to break down traits of complex inheritance into individual loci, even those under a significant environmental influence. The procedure is equally workable with dominant or recessive traits and can be used to accelerate introgression of desired genes into a commercially acceptable cultivar. As used herein, "plants" includes all forms of plant life, such as crop plants, mushrooms and fungi, ferns, trees, flowers and so on. These examples are not intended to be limiting but are merely illustrative of the wide applications of the invention.

BRIEF DESCRIPTION OF THE DRAWINGS

FIG. 2 illustrates the correlation between colorimetric absorbance values (2TD) and various RFLP loci on three linkage groups. Numbers in parentheses refer to correlation coefficients, numbers above lines indicate locus identification, and numbers below lines indicate recombination fractions (experiment 1).

FIG. 6 is a representations of a tomato genetic linkage map of RFLP loci; circled loci are those screened for association with expression of water-use efficiency.

DETAILED DESCRIPTION OF THE INVENTION

Figure 1A:
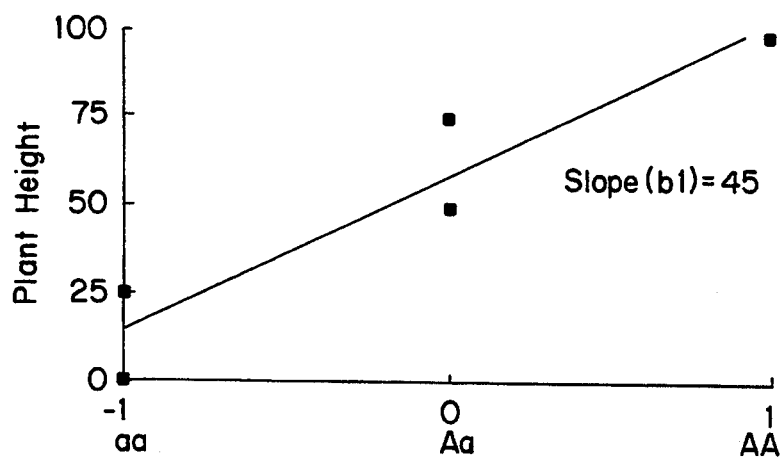
FIG. 1A shows the regression between genotypes at RFLP locus "A" and plant height, identifying an additive gene.

The invention typically involves genetic linkage maps constructed with RFLP technology and the use of RFLP probes to correlate those probes with Quantitative Trait Loci (QTL) and the degree of inheritance of particular multigenic traits.

In one embodiment, a plant source (designated $P_1$) having a desired multigenic trait—for example, increased height—is recovered and crossed with a second plant (designated $P_2$) having essentially or substantially opposite characteristics, that is, decreased height. Heterozygote plants from the $F_1$ population are selfed to create a segregating ($F_2$) plant population which exhibit a gradient with respect to height, i.e., with respect to the degree of expression of the multigenic or quantitative trait of interest.

Quantitative values for the trait of interest (height) are determined and assigned to each individual parent plant, $F_1$ population plant, and $F_2$ segregation plant and a genomic DNA sample from each plant is prepared for Southern blotting. Following preparation for a Southern blot—which may be constructed to contain, for example, DNA from 25 to 50 or more different $F_2$ plants—an RFLP probe is randomly chosen or selected from an RFLP genetic linkage map and hybridized to create the blot. Additional Southern blots are constructed using other RFLP probes. As indicated above, the RFLPs to be used for this purpose, i.e., the indirect selection of a QTL, may but need not be randomly chosen. They can be selected in systematic fashion from the RFLP genetic linkage map. For example, for a trait of completely unknown location, several spaced RFLPs from each of the 10 chromosomes of maize may be selected for Southern blot testing for the location of DNA associated with a desired height. Alternatively, of course, all mapped RFLPs may be used.

Following these Southern blot constructs, a matrix may be prepared having an identification of each plant that has been tested, followed by its quantitative trait measurement (height) and the genotype as revealed by each RFLP probe tested. Typically, only three genotypes will be seen: $P_1$, $P_2$ and $F_1$, the latter being heterozygous and having one chromosome from each parent. Thus, from the matrix all plants can be grouped into one of three RFLP genotypic categories: $P_1P_1$, $P_1P_2$ or $P_2P_2$. If, with one or more RFLPs, the so-grouped plants, when averaged, all show approximately equal expression of the trait of interest, i.e., the average height of plants in all groups is about the same, that RFLP is deemed noninformative. In other words, there was no association between the trait of interest and that particular RFLP or RFLPs. The genotype of the plant at the location of the RFLP was not relevant to the trait of interest.

Another RFLP, however, may show association with height. For example, the average height of the maize plants, respectively, in each of the $P_1P_1$, $P_1P_2$ and $P_2P_2$ groups for a different RFLP, respectively, may be 3 feet, 4 feet and 5 feet. With this information, it may be presumed that this RFLP, as revealed by the degree of its correlation to the $P_2P_2$ genotype, hybridizes to maize DNA in the area of a gene for height.

In the above-described manner, it is possible to review results from a first group of RFLP probes used to screen for association to the trait of interest. Use of an RFLP genetic linkage map allows the selection of further RFLPs to be tested on an objective, rather than random, basis. Correlation may be improved by testing RFLPs located on either side of that RFLP or RFLPs which initially showed the strongest association. Once the best probe or probes are identified they may then be utilized, by way of example, in a breeding program to select plants having a desired height.

It is to be noted, of course, that in a multigenic system, there may be three, four, or more different genes contributing to one trait. In such a situation there may, therefore, be many different quantitative expressions of that trait and no one gene can account for, or be relied upon to predict, that expression. We have further determined that the relative importance of each correlating RFLP can be determined. Particular values can be assigned to those RFLPs and utilized in a mathematical model to assist in predicting the degree of trait expression in a particular plant.

The following is a hypothetical example of the analysis of RFLP data, and the development of a predictive model relative to identification, localization and introgression of a quantitative trait, plant height, assuming the possession of RFLP data on 3 loci. A matrix or table which includes the necessary raw data is presented in Table 1. In this hypothetical, plant height ranges from 0 to 100 units. The genotypic classes for 3 RFLP loci are also presented.

The first objective of the analysis to determine which, if any, of the 3 RFLPs are associated with the expression of plant height. To determine the relative importance of any individual RFLPs, a simple regression of plant height by genotypic value is used. This can be referred to as the average effect of an allelic substitution, as it enables observation of how the value of plant height changes as "A" alleles are substituted for "a" alleles. The regression for RFLP "A" is presented in FIG. 1a. Here we see that the average height of all plants which have a genotype of aa is approximately 12.5 units. Likewise, for Aa individuals, the average is approximately 62.5 units and, for AA individuals, the average expression of plant height is 100 units. The regression of plant height by the genotypic values provides a least squares regression line, which in this hypothetical has a slope of 45. "Least squares" refers to the fact that in this line the squares of the deviations of the points from the regression line are minimized, i.e., this line represents the "best fit" for the 5 points. The slope of the line can be interpreted as saying that each time an "A" allele is substituted for an "a" allele, plant height increased 45 units. The conclusion to be drawn from the regression of RFLP "A" is that it is strongly associated with the expression of plant height or that a gene(s) very closely linked to RFLP "A" is important in the expression of plant height.

Figure 1B:
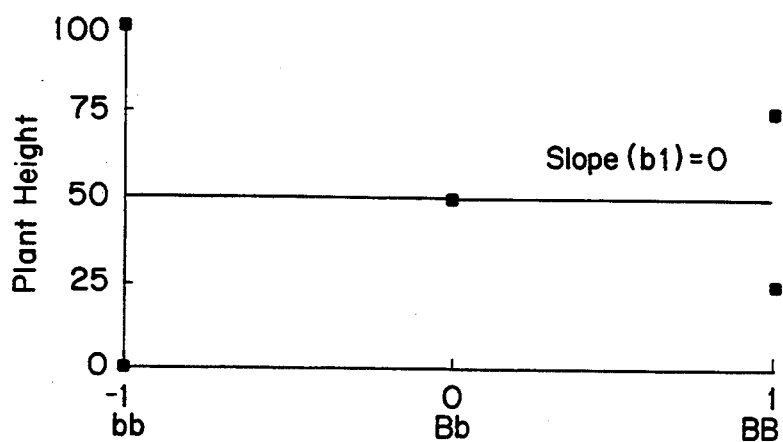
FIG. 1B is a graphical depiction of the relationship between genotypes at RFLP locus "B" and plant height when the locus is not associated with plant height.

In contrast, RFLP "B" is not associated with the expression of plant height (FIG. 1b). In this case, the average expression of plant height is 50 units regardless of the genotype of RFLP "B". Hence its regression line has a slope of 0 and the RFLP is deemed noninformative.

Figure 1C:
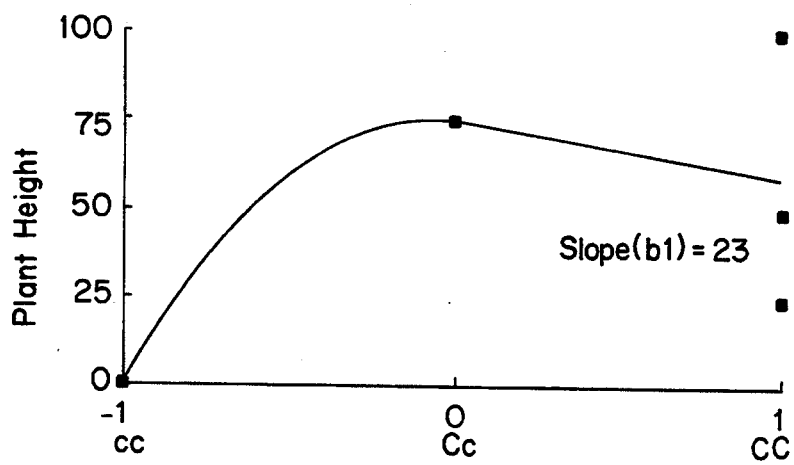
FIG. 1C shows the relationship between genotypes at RFLP locus "C" and plant height, identifying a non-additive gene.

RFLP "C" (FIG. 1c) is similar to "A" in that plant height is clearly associated with the genotype. The slope of the line through the observed data points is not simply linear, however, but rather the "best fit" regression line is a curve (quadratic). The reason RFLP "C" is different from "A" is that "C" reflects a gene with dominance type gene action compared to the additive gene action of "A". RFLP "C" illustrates complete dominance, i.e., the average plant height of genotype Cc is essentially equivalent to that of the homozygote class CC. Thus, although RFLP "C" is not additive in gene action, it is still identified as being important in the expression of plant height.

These three hypothetical RFLPs illustrate the most common associations between RFLPs and traits of interest. It is to be emphasized that the resolution possible through RFLP analysis permits not only the identification of the RFLP associated with the expression of a trait, but also permits the identification of the type of gene action (additive or dominance). Thus, in this hypothetical, the conclusion is that of the three RFLP evaluated, "A" is important with additive gene action and "C" is important with dominance gene action. "B" was not associated with expression of plant height and would not be considered in further analysis.

Information similar to that obtained from the RFLP plots of plant height by genotypic classes can also be gleaned from an analysis of variance, such as that shown in Table 2. The objective of an analysis of variance is to partition the total phenotypic variance into specific sources. In this case, the logical question is to ask how much of the total variation for plant height can be attributed to differences among genotypes and how does the magnitude of that variance compare to the error (deviations from regression).

In the case of RFLP analysis, there are three different genotypic classes, i.e., AA, Aa and aa. Among three classes there are two possible contrasts and, hence, there are 2 degrees of freedom among genotypic classes. Moreover, the two possible contrasts among genotypes can be specifically partitioned into linear and quadratic sources, each with one degree of freedom. The linear contrast would have the values $-1$, 0 and $+1$ for the three genotypic classes AA, Aa and aa, respectively. This effectively compares the difference between the AA class and the aa class, i.e., the parental classes. The values for the quadratic contrast are 1, $-2$ and 1 for the three genotypic classes and, therefore, compare the difference between the mean of the parental AA and aa classes to the heterozygote class Aa.

The error, or deviation from regression, reflects the failure of the observed points to be exactly on the regression line. In the case of RFLP "A" we can observe that the mean square for the linear contrast is approximately 100 times larger that of the quadratic contrast and about 10 times larger than the error mean square. The magnitudes of the mean squares from the analysis of variance indicates that linear regression can account for the majority of the variance among the plant heights. The $r^2$ (coefficient of determination) value can be defined as the sums of the linear and quadratic mean squares divided by the total phenotypic variance (the total sums of squares of deviations from mean). The $r^2$ value for "A" indicates that 89% of the observed variance for plant height can be explained as due to differences among RFLP "A" genotypic classes. Similarly, the analysis of variance for RFLP "B" indicates that none of the variance for plant height can be explained due to differences among genotypic classes. The analysis of variance for RFLP "C" indicates that 53% of the variance can be explained due to differences among genotypic classes and that both the linear and quadratic contrast are important. Thus, the relative magnitudes of mean squares from the analysis of variance provides a description of the relationship between RFLPs and plant height. The conclusions coincide with those obtained from observation of the plots of plant height by genotypic classes shown in FIG. 1.

The means for each genotypic class are also presented in Table 2. These means represent the average phenotypic performance for each of the 3 genotypic classes. For RFLP "A", the mean of the parent 1 class (aa) is 12.5, the mean for the heterozygous class (Aa) is 62.5, and the mean for the homozygous parent 2 class (AA) is 100 plant height units. The linear regression line slope (b1) is also presented for each RFLP. Thus, the linear regression of plant height on genotypic classes for RFLP "A" is 45. This, as noted above, can be interpreted as indicating that each time an "A" allele is substituted for an a allele that plant height will increase 45 units. The slope thus permits comparisons among RFLPs and helps to identify those RFLPs most strongly associated with the expression of a trait of interest.

Once the RFLPs most strongly associated with the expression of a trait are identified, the effects of each RFLP may be combined into a multiple regression model which will permit prediction of expression of the trait of interest based on knowledge of the genotypes of specific RFLP. The effects of each RFLP are not strictly additive because the effects of RFLP may be correlated. For example, in this case, RFLP "A" and "C" may each provide some unique information, but part of the information provided by one RFLP may also be provided by another. Thus, the average effects of allelic substitutions may not be simply added together to provide a predictive model.

The general form of a useful multiple regression predictive model is shown below:

$$y = \mu + b_1 \text{ (genotype of RFLP locus 1)} + b_2 \text{(genotype of RFLP locus 2)}$$

where y is the predicted expression of a trait, $\mu$ s the weighted mean expression of the trait for the population, $b_1$ is the coefficient associated with a specific RFLP and so on. The genotype of a RFLP will be $-1$, 0 or 1 for genotypic classes AA, Aa and aa if the RFLP is additive (linear), or 1, $-2$ or 1 if the RFLP is quadratic (non-additive).

Determination of the "best" multiple regression model requires an interative process of substitution of RFLPs into and out of the model and the evaluation of interaction (epistatic) effects of RFLPs. For example, if two independent genes act together to provide expression of a trait, the genotypic class may involve the products of linear and/or quadratic genotypic values. The process for determination of the "best" multiple regression model can be done using stepwise regression procedures or by comparison of partial and sequential sums of squares from the regression models.

For example, in the present hypothetical, the logical RFLPs to include in the model would be the linear contrast for RFLP "A" and both the linear and quadratic contrasts for RFLP "C". The partial and sequential sums of squares (SS) for a model including RFLP A and C are the following:

| Source | sequential SS | partial SS |
|---|---|---|
| linear "A" | 5580 | 2812 |
| linear "C" | 62 | 236 |
| quadratic "C" | 503 | 503 |

The magnitudes of the sums of squares indicates that linear "A" is the most important determinate in explaining the variance for plant height. However, the reduction in partial SS (2812) vs. sequential SS (5580) for linear "A" suggests that much of the effect of linear "A" is accounted for by the linear and quadratic effects of "C". It should be noted that if the effects of each locus were completely independent there would be no differences in the partial and sequential sums of squares. Changes in the magnitudes of these sums of squares in an analysis of variance indicates that the effects of the different RFLP are correlated.

The iterative process of substituting linear and quadratic contrasts for different RFLPs can continue until a final predictive model is constructed. The objective of the model is to maximize the $r^2$ (coefficient of determination) value using as few RFLP as possible as predictive variables. The final model will generally eliminate RFLP which might flank a particular gene of interest because both RFLP will typically be contributing the same information. In addition, the final model might contain effects with reflect interactions between RFLPs.

In the present hypothetical, the next step in the process of model building might be to eliminate the linear contrast for RFLP "C". The results of this model are the following:

| Source | sequential SS | partial SS |
|---|---|---|
| linear "A" | 5580 | 5127 |
| quadratic "C" | 328 | 328 |

The general agreement in magnitude between partial and sequential SS suggest that the effects of linear "A" and quadratic "C" are relatively independent. The $r^2$ value for this model is 0.95. Thus, 95% of the variance for plant height can be explained as due to differences among genotypic classes at RFLP "A" and "C". The final prediction equation would, therefore, be written as follows:

plant height = 61.4 + 43 (linear code RFLP A) − 7.0 (quadratic code for RFLP C).

Thus, if the genotypes of RFLP A and C are known for a particular plant, the height of that plant can be predicted without having to measure its height following growth to maturity. In a breeding program, the breeder can analyze the genotypes of specific RFLP of seedling plants grown in a greenhouse during the winter and need only evaluate those plants predicted to have the desired plant height in the field the following summer.

TABLE 1

| | Hypothetical Raw data | | | | | |
|---|---|---|---|---|---|---|
| Genotype Observed | "A" (Linear Code) | | "B" (Linear Code) | | "C" (Linear Code) | (Quadratic Code) | Plant Height |
| 1 | AA | 1 | bb | −1 | CC | 1 | 1 | 100 |
| 2 | aa | −1 | bb | −1 | cc | −1 | 1 | 0 |

TABLE 1-continued

| | Hypothetical Raw data | | | | | | | |
|---|---|---|---|---|---|---|---|---|
| Genotype Observed | "A" (Linear Code) | | "B" (Linear Code) | | "C" (Linear Code) | | (Quadratic Code) | Plant Height |
| 3 | Aa | 0 | BB | 1 | C | c | 0 | −275 |
| 4 | Aa | 0 | Bb | 0 | CC | 1 | 1 | 50 |
| 5 | aa | −1 | BB | 1 | CC | 1 | 1 | 25 |

TABLE 2

Analysis of Variance

| | | RFLP locus | | |
|---|---|---|---|---|
| Source of Variance | Degrees of Freedom | A | B | C |
| | | Mean Squares | | |
| Genotype | 2 | | | |
| linear | 1 | 5104 | 0.0 | 2552 |
| quadratic | 1 | 44 | 0.0 | 1575 |
| Error (deviations from regression) | 2 | 625 | 6250 | 1458 |
| $r^2$ | | 0.89 | 0.0 | 0.53 |
| Genotypes | (code) | Means | | |
| Homozygous Parent 1 | (−1) | 12.5 | 50 | 0 |
| Heterozygote | (0) | 62.5 | 50 | 75 |
| Homozygous Parent 2 | (+1) | 100.0 | 50 | 58 |
| Slope(b1) | | 45 | 0 | 23 |

The breeding value of an RFLP as an indirect selection criteria is a function of the additive genetic correlation between the RFLP marker and a QTL. This genetic association is presumed to be due to linkage disequilibrium rather than due to pleiotropism. The problem of recombination between an RFLP and an associated QTL can be minimized if two RFLP are identified which flank the QTL. In that instance, the probability of a double crossover would be, assuming no interference, the product of their recombination frequencies. Nevertheless, localizing a target QTL between a pair of linked RFLP can be problematic, and the complexity of the analyses increased. One possible solution to the analysis using flanking RFLPs is to use multivariate analysis and derive one or more orthogonal vectors which include information from linked (correlated) RFLP loci. Alternatively, if crossovers are detected between the two flanking RFLPs for specific entries, the RFLPs linked to the QTL can be determined and information from the other RFLP discounted.

The rate of gain from indirect selection in a population is a function of the magnitude of the phenotypic variance of the desired trait, the selection differential, the heritability of the indirect criteria, and the genetic correlation between the direct and indirect criteria. Indirect selection for RFLPs will have an advantage over direct selection if the heritability of RFLPs is higher than the desired character and the additive genetic correlation between them is high.

The "heritability" of the RFLP phenotype is 1.0, i.e., genotype=phenotype. Hence, if the correlation between RFLPs and the desired trait is greater than the heritability of the desired trait, then RFLP-facilitated selection can be advantageous. In the evaluation of 2-tridecanone ("2TD")mediated insect resistance in tomatoes, for example, the development of the colorimetric assay has contributed to increased efficiency of selection. In the following Example 1, the correlation between observed and predicted colorimetric absorbance values of 2TD was 69% utilizing four correlating RFLPs. The magnitude of this correlation coefficient suggests that indirect selection for hirsutum alleles at the selected RFLPs will result in a correlated response towards increased colorimetric absorbance values. RFLP analysis can also provide a complete genotypic classification of individuals as seedlings in segregating generations, leading to especially useful information in a backcross breeding program, where superior genotypes can be identified prior to flowering.

As noted above, quantitative differences between genotypes are usually, but not always, influenced by genes at many loci, the effects of which are small in relation to the variation arising from other causes (Falconer, D.C., "Introduction to Quantitative Genetics" (2d Edition 1981)). Consequently, the individual genes involved in the expression of a quantitative trait are difficult to identify and Mendelian analysis cannot be applied. Id. Quantitative genetic analysis has therefore focused on estimation of breeding value which is the sum of the effects of the alleles at many loci. Nevertheless, a basic premise of quantitative genetics is that the laws which govern the inheritance of quantitative loci are the same as those which govern qualitative loci. The magnitude of the individual allelic effects which can be resolved through RFLP analysis will be a function of experimental error and recombination frequencies. As RFLP maps are developed which more completely saturate the genome, identification of more loci with smaller individual effects should be possible. Thus, RFLP analysis also offers the opportunity to determine the effects of individual loci (alleles) with major effects, and thereby to reduce the analysis of complex quantitative traits to classical Mendelian segregation ratios of individual alleles.

By way of example, field and laboratory determination of quantitative differences in insect resistance is often very expensive in terms of time and resources in most plant species, and genetic markers could greatly facilitate the determination of the breeding value of an individual genotype. In Example 1, noted above, 4 RFLPs on 3 linkage groups were found to be associated with expression of 2TD. In a previous study of an $F_2$ population derived from a cross between a L. hirsutum acession (LA 407) and an L. esculentum line (M82-1-8), 5 independent marker loci, 3 isozyme and 2 morphological, were found to be associated with expression of 2TD. Zamir et al., Euphytica 33:481–488 (1984). The morphological markers were the genes (sp) controlling determinant growth habit, and (sti) responsible for the presence of stipules at the base of the leaves, neither of which was segregating in the $F_2$ population evaluated in this study. If the 3 isozyme markers are polymorphic in the $F_2$ population used in this study and they are linked to the same QTL as the 3 RFLP, then isozyme markers could be used to predict 2TD. Nevertheless, because of the larger number of informative RFLPs available in population of interest, it is likely that an RFLP could be found more closely linked to a target QTL than isozyme or morphological markers. The results in Example 1 demonstrate that RFLPs can be used as indirect selection criteria to increase the frequency of favorable alleles associated with quantitatively inherited traits. In addition, other RFLPs not linked to a target QTL might also be used in a breeding program to select against the genotype of the donor parent. This combination of selection criteria applied in a backcross breeding program will facilitate the introgression of desirable genes and traits from wild relatives, and concurrently permit the rapid recovery of the genotype of the desirable recurrent parent.

The following Examples are set forth to assist in understanding the invention and should not, of course, be construed as specifically limiting the invention described and claimed herein. Such variations of the invention which would be within the purview of those in the art, including the substitution of all equivalents now known or later developed, are to be considered to fall within the scope of the invention as hereinafter claimed.

EXAMPLE I

The wild tomato *L. hirsutum f. glabratum* C. M. Mill P.I. 134417 (hirsutum) has been reported to be resistant to a wide range of arthropod pests of the cultivated tomato. The principal toxic factor has been identified as 2-tridecanone (2TD) which is localized in the tips of the glandular (type VI) trichomes which cover the foliage. In an analysis of an $F_2$ population derived from a cross between hirsutum P.I. 134417 and an *L. esculentum* (esculentum) cultivar "Manapal", it has been suggested that a minimum of 3 genes are involved in the inheritance of 2TD expression. Fery et al., *Hort. Sci.*, 18:169 (1983). Moreover, in a cross between a *L. hirsutum* accession, LA 407, and a tomato breeding line, M82-1-8, 2 morphological markers and 3 isozyme loci were found to be associated with expression of 2TD. Zamir et al., supra.

The following procedures were designed to identify RFLPs associated with QTLs affecting expression of 2TD-mediated insect resistance. Additional objectives were to determine the gene effects of the RFLPs and to develop a predictive model for 2TD-mediated insect resistance using the 3 genotypic classes at each RFLP as predictor variables.

A tomato, *Lycopersicon esculentum*, L. cultivar, Manapal, and a selection from the non-domesticated tomato species *L. hirsutum f. glabratum*, P.I.134417, were obtained from Dr. George Kennedy, North Carolina State University, Raleigh. The $F_1$ hybrid was obtained using "Manapal" as the female parent. The $F_1$ was then self-pollinated to produce the $F_2$ seed used in all experiments.

In the first experiment, a group of test plants, which included parental, $F_1$ and a random sample of 100 different $F_2$ plants, were evaluated each month over a nine month period. All plants were grown in a greenhouse where temperatures were maintained between 15° and 25° C. and light intensity was supplemented to a minimum of 400 $\mu$mole photon $m^{-2}s^{-1}$ for 18 hours per day. When the plants in each group developed at least 4 true leaves, 1 $cm^2$ leaf disks were sampled from 5 leaflets on each of the 3 largest leaves. The leaf disks were bulked and evaluated colorimetrically for 2-tridecanone (2TD) expression.

The colorimetric assay developed for 2-tridecanone is based upon the reaction of carbonyl groups in solution with 2,4-dinitrophenylhydrazine, which produces a wine red color in the presence of a base. Nienhuis, et al., *Hort. Sci.* (abstract) 20:590 (1985). In a population of 36 random $F_2$ plants derived from a cross between *L. hirsutum f. glabratum* P.I. 134417 and the *L. esculentum* cultivar "Manapal" the correlation between the absorbance values obtained using the colorimetric assay and the amount of 2TD per unit leaf area determined using gas chromatography was 0.95. Id. The absorbance value for each $F_2$ plant in a group was determined as the average absorbance at 480, 510, and 540 nm. Because 2TD has been found to be significantly more abundant in the foliage of hirsutum plants grown under long-days compared to short-days, the colorimetric absorbance values of individuals in each of the 9 groups were adjusted to a percentage of the hirsumtum parent. From each of the 9 groups, 7 to 10 plants were chosen which represented a wide range of absorbance values. A total of 74 plants were selected and maintained in the greenhouse.

Cuttings from each of the 74 test plants were rooted and grown in a uniform greenhouse environment and later reevaluated colorimetrically for 2TD. Sufficient leaf tissue was harvested from each plant to provide a 5 g dry weight sample for RFLP analysis. The procedures for plant DNA preparation, restriction enzyme digestion, Southern blotting, preparation of radioactive probes, and hybridization have been described in a previous publication (Helentjaris et al. I). A further description of methodologies used in the selection of useful marker clones in a tomato population is detailed in a companion publication (Helentjaris et al. II).

A two phase screening process was used to identify the RFLPs associated with expression of 2TD. In the first screen, a sample 36 RFLPs were evaluated on all 74 test plants. The 36 selected RFLPs were chosen to be approximately 10 to 20 centimorgan map units apart with at least one RFLP selected from each of the 20 defined linkage groups. Helentjaris et al. II. In the second screen, flanking RFLP markers on linkage groups identified in the first screen to be associated with expression of 2TD were evaluated. In the second screen, 46 $F_2$ test plants, which represented the widest range of 2TD expression, were used. The degree of association between individual RFLPs and absorbance values for 2TD were indicated by the magnitude of the linear correlation of colorimetric absorbance values with hirsutum allele frequency.

In the second experiment, parental, $F_1$, and $F_2$ plants were grown in Conviron growth chambers at 20° C. day and 15° C. night temperatures with a constant 16 hr. photoperiod. To facilitate laboratory analysis, the test plants were planted in 6 blocks of 25 plants each, which included parental, $F_1$ and 22 $F_2$ plants. At the three leaf stage 5 leaf disks were sampled, using the same procedure as in the previous experiment, and evaluated colorimetrically for 2TD expression. Based on these analyses, 16 $F_2$ plants were selected from each block which represented the widest range of expression for colorimetric absorbance values. Five additional 1 $cm^2$ leaf disks were sampled from the margins of leaflets from each of the 3 largest leaves on each selected $F_2$ plant and the number of type VI trichomes/leaf disk determined. Sufficient leaf tissue was harvested from the 96 selected $F_2$ plants to provide at least 5 g dry weight for RFLP analyses. Procedures for DNA extraction and Southern blotting were the same as outlined in the above experiment. Two closely linked RFLP loci from regions on each of the three linkage groups identified in the first experiment as being associated with QTLs affecting colorimetric absorbance (2TD) were used as probes in the second experiment.

The number of $F_2$ individuals in each of the three genotypic classes, homozygous esculentum (e/e), heterozygous (e/h) or homozygous hirsuteum (h/h) at each RFLP was determined and chi-square goodness-of-fit statistics calculated for 1:2:1 Mendelian segregation ratio. Linear and quadratic contrasts among the three genotypic classes at each RFLP were used to predict the degree and type of gene effect for colorimetric absorbance (2TD) and trichome density. Main effects of the RFLPs associated with colorimetric absorbance, and first and second order interactions among them, were fit in multiple regression model to maximize the coefficient of determination.

In experiment 1 the correlation of colorimetric absorbance values between individuals in each of the 9 groups and the subsequent evaluation of cuttings in a uniform environment was 79% (data not shown). The magnitude of this correlation coefficient suggests that genotype-by-environment interactions for the colorimetric absorbance values were small. Hence, the mean of the two colorimetric evaluations was used in the analysis.

The magnitude of the correlation coefficients between the three genotypic classes, e/e, e/h and h/h, for each RFLP and colorimetric absorbance values in experiment 1 suggested that regions on three different linkage groups, C, D and I, were associated with the expression of 2TD (FIG. 2). The RFLPs on each linkage group with the highest correlation to the colorimetric absorbance values were C56, D68 and I38. The magnitude of the correlation coefficients for flanking RFLPs tended to decrease with increasing map distance from the RFLP with the highest correlation coefficient. Two RFLPs, C56 and D68, were located on the ends of linkage groups, and it is possible that the associated QTL was not flanked on both sides by identified RFLPs. When other RFLPs are localized adjacent to C56 and D68, determination of whether they are more highly correlated with the QTLs affecting expression of 2TD than C56 and D68 will be possible. Nevertheless, the results of experiment 1 provided an initial identification of 3 chromosomal regions associated with the expression of colorimetric absorbance (2TD).

Figure 3:
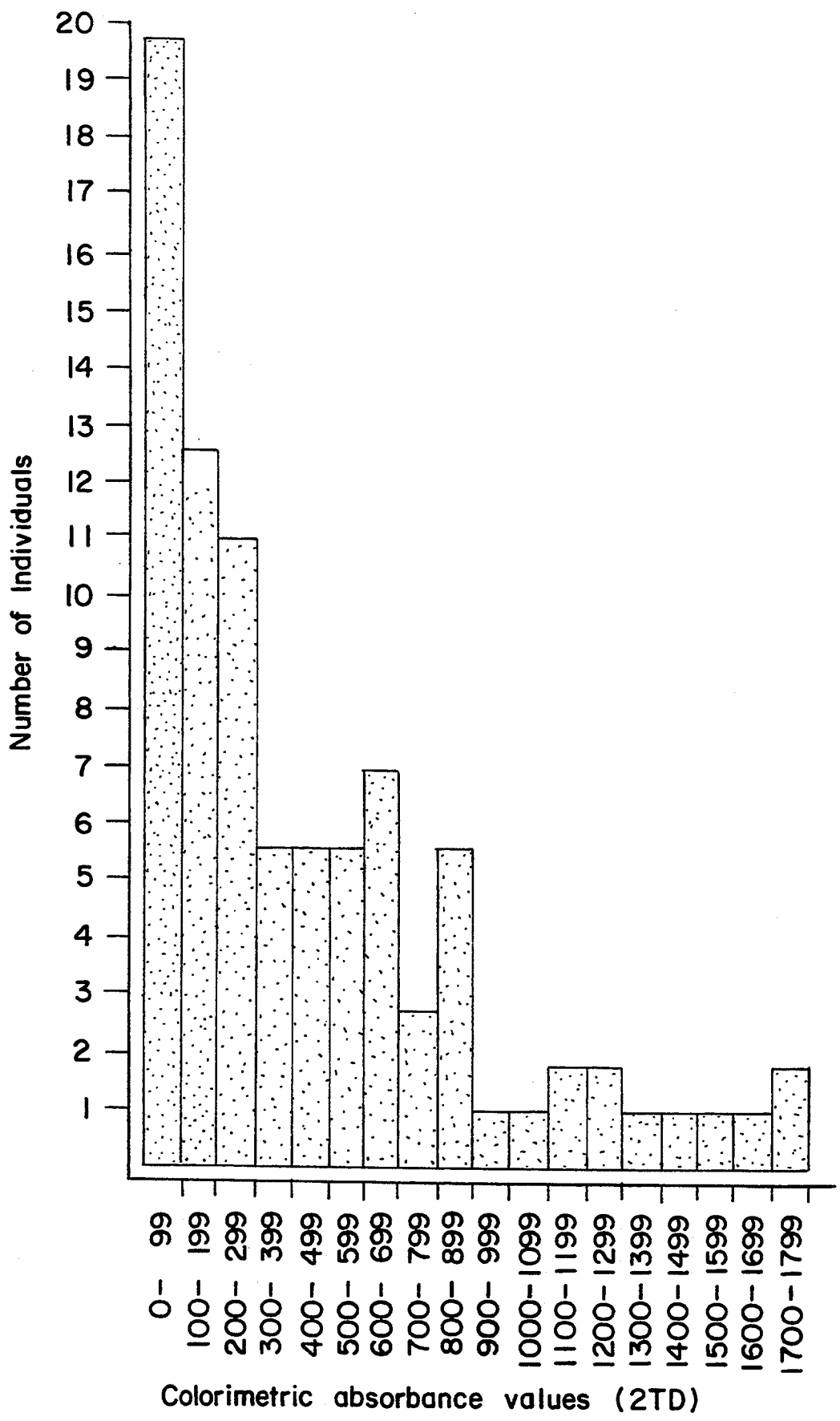
FIG. 3 shows the distribution of colorimetric absorbance values (2TD) for an $F_2$ population derived from a cross between P.I. 134417 and Manapal (experiment 2).

In experiment 2, genotypic frequencies for the 2 RFLPs on each of the 3 linkage groups all deviated from the expected Mendelian 1:2:1 ratio (Table 3). Deviation from expected Mendelian segregation in populations derived from crosses between *L. esculentum* and *L. hirsutum f. glabratum* accessions have previously been observed, Zamir et al., *Genetics* 101:129–137 (1982), and have been attributed to gametic selection under low temperatures for gametes containing hirsutum chromosomes. In experiment 2 the tendency for $F_2$ individuals to have a higher gene frequency for hirsutum alleles may also have been aggravated by selection for the 16 $F_2$ individuals within each group of 22 which had low absorbance values and which were, therefore, more likely to have esculentum alleles. In spite of higher gene frequency for hirsumtum alleles, ranging from 0.67 to 0.75 (data not shown), the distribution of colorimetric absorbance value, for the 96 selected $F_2$ individuals used in experiment 2 was highly skewed towards low absorbance values (FIG. 3). The effect of this shift in gene frequency was to reduce the variance among genotypic classes at each RFLP, which would otherwise be maximized at a gene frequency of 0.50, concurrently reducing the magnitude of the covariance between gene frequency and phenotypic value.

The analyses of variance among the 3 genotypic classes was partitioned into two orthogonal contrasts (Table 4). The linear contrast was significant for all RFLPs except RFLP C56, in which the quadratic contrast was significant. The coefficients of determination for simple regression ranged from 0.05 for the RFLP on linkage group C to 0.17 for RFLP D81. The average effect of an allelic substitution was calculated as the linear regression coefficient of phenotypic value (colorimetric absorbance values) on gene frequency. These results suggest that the type of gene action associated with expression of 2TD was predominantly additive, except for the QTL linked to RFLP C56, in which gene action was non-additive.

2-tridecanone is localized in the tips of type VI glandular trichomes in hirsutum, and the amount of 2TD per unit area of foliage is the product of the number of trichomes and amount of 2TD per trichome. Thus, a component of 2TD expression is the number of trichomes per unit area. Because the number of trichomes per unit area is a function of leaf development (size), the trichome counts per leaf disk were adjusted by analysis of covariance for the size of the leaflet from which each disk was punched (data not shown). In the analyses of variance of adjusted trichome number, the mean square for the linear contrast for RFLP D68 was the largest (Table 5). This suggests that of the RFLPs associated with expression of 2TD, D68 may be primarily associated with the expression of type VI trichome density.

The development of a model to predict 2TD expression based on the genotype of RFLPs was complicated by the high correlation of genotypic values between the pairs of RFLP on each of the 3 linkage groups. To avoid the problem of multicolinearily (or high correlation) between linked RFLP, the linear contrast of the RFLP with the largest effect on each of 3 linkage groups was included in the regression model (Table 6). In addition, the quadratic contrast for RFLP C56, which is orthogonal to the linear contrast for RFLP C22, was included in the regression model. The regression model, which included main effects of each of the 4 RFLPs as well as significant first and second order interactions, accounted for over 38% of the total phenotypic variance for absorbance values (Table 6). The interactions observed among the linear contrasts for RFLPs C22, DS1 and I28 would suggest that additive by additive epistatic interactions among the linked QTL loci are important in the expression of colorimetric absorbance values (2TD).

Figure 4:
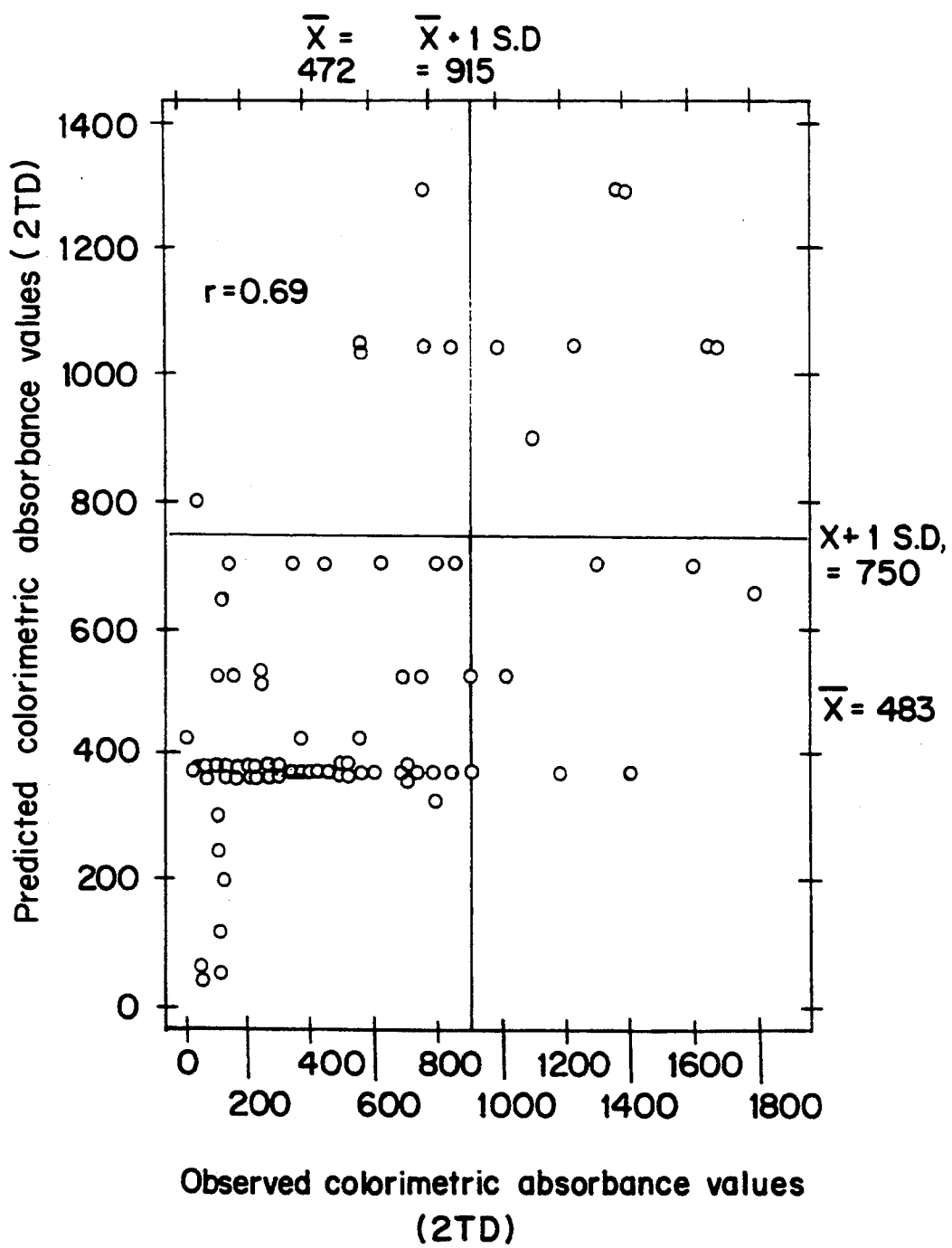
FIG. 4 portrays the observed versus predicted values for colorimetric absorbance (2TD).
Figure 5:
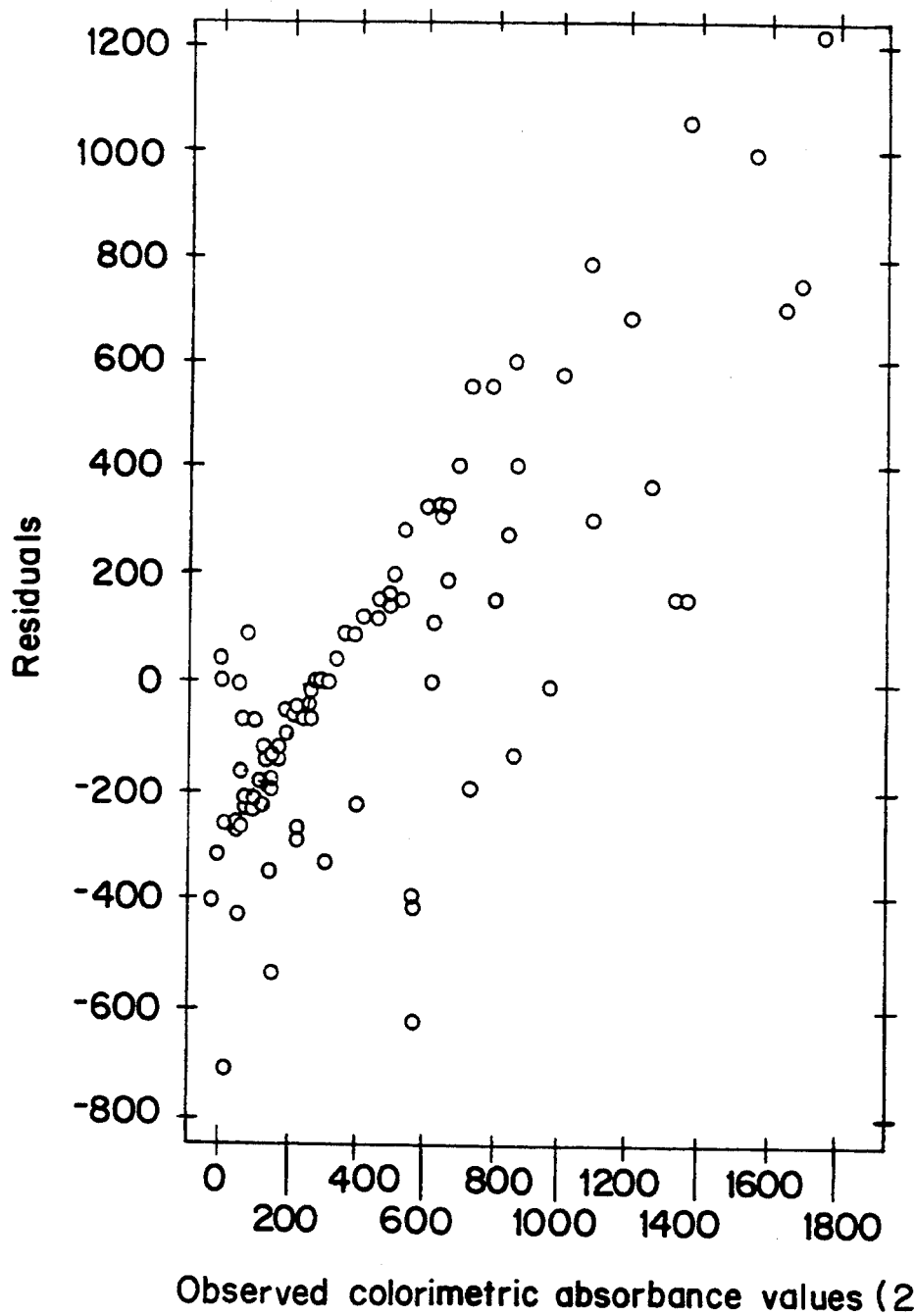
FIG. 5 is a plot of residual versus observed colorimetric absorbance values (2TD).

The plot of observed vs. predicted absorbance values revealed that 39 of the 96 $F_2$ individuals in the population had absorbance values above the observed mean. 23 of the 39 had been predicted to be above the mean based on the regression model (FIG. 4). The plot of observed vs. predicted colorimetric absorbance further indicated that the multiple regression model would better predict individuals with low rather than high colorimetric absorbance values. Inspection of residual plots revealed that the errors associated with the prediction of individuals with high absorbances values were much larger than those for low value individuals (FIG. 5). Moreover, the nonrandom pattern of the residuals suggested a systematic deviation.

If the failure of RFLPs to better predict observed phenotypes were due to recombination between the marker RFLP's and their associated QTLs the pattern of residuals would be expected to be a random scatter about a mean of zero. In contrast, if the failure of RFLPs to better predict the phenotype were due to the inability to identify an RFLP locus associated with a QTL with major effects, then the residuals would be expected to be larger for individuals which were observed to be high in phenotypic value. Inspection of the residual plots for experiment 2 suggest that one or more additional QTLs, which were not identified as linked to the RFLPs may be associated with expression of 2TD.

TABLE 3

Genotypic frequencies for 2 RFLP on each of 3 linkage groups (experiment 2).

| Genotype | C22 | C56 | D81 | D68 | I38 | I28 |
|---|---|---|---|---|---|---|
| e/e | 6 | 6 | 5 | 6 | 5 | 5 |
| e/h | 47 | 47 | 53 | 49 | 37 | 36 |
| h/h | 42 | 42 | 38 | 37 | 52 | 53 |
| $X^2$ | 27.3** | 27.3** | 27.7** | 21.3** | 51.3** | 54.2** |

* e/e = esculentum homozygote, e/h = heterozygote, and h/h = hirsutum homozygote
** indicates signficant deviation from expected 1:2:1 segregation ration at 0.01 level.

TABLE 4

Analysis of variance mean squares and genotypic means for colorimetric absorbance values (2TD) for 2 RFLP on each of 3 linkage groups (experiment 2).

| Source | d.f. | C22 | C56 | D81 | D68 | I38 | I28 |
|---|---|---|---|---|---|---|---|
| | | | | Mean squares | | | |
| Geneotypes | 2 | | | | | | |
| Linear | 1 | 678968* | 125601 | 3042549* | 1962483* | 1802941* | 1839632* |
| Quadratic | 1 | 10476 | 218063* | 2121063 | 1042812 | 193528 | 686236 |
| Dev. from Regression | 92 | 191785 | 191162 | 166195 | 176424 | 182991 | 182597 |
| $r^2$ | | 0.05 | 0.05 | 0.17 | 0.11 | 0.08 | 0.10 |

| Geneotype* | | | Means Number | | | |
|---|---|---|---|---|---|---|
| e/e | 114 | 114 | 200 | 207 | 86 | 86 |
| e/h | 464 | 525 | 338 | 366 | 371 | 372 |
| h/h | 538 | 474 | 694 | 639 | 587 | 591 |
| Average effect of an allelic substitution + | 140 + 75 | 60 + 76 | 310 + 72 | 245 + 73 | 232 + 73 | 234 + 74 |

*Significant at 0.05 level.
+See Table 1 for an explanation of genotype symbols.
+Linear regression coefficient and standard error, respectively.

TABLE 5

Analyses of variance mean squares and genotypic means for number of type VI trichomes/cm² for 2 RFLP on each of 3 linkage groups (experiment 2).

| Source | d.f. | C22 | C56 | D81 | D68 | I38 | I28 |
|---|---|---|---|---|---|---|---|
| | | | | Mean squares | | | |
| Geneotypes | 2 | | | | | | |
| Linear | 1 | 711.9 | 822.1 | 384.4 | 1597.7+ | 1022.0 | 1093.7 |
| Quadratic | 1 | 440.2 | 344.3 | 71.5 | 417.1 | 355.3 | 404.4 |
| Dev. from Regression | 92 | 484.4 | 484.5 | 509.1 | 498.1 | 510.9 | 511.6 |
| $r^2$ | | 0.06 | 0.06 | 0.01 | 0.04 | 0.02 | 0.02 |

| Geneotype+ | | | Means Number | | | |
|---|---|---|---|---|---|---|
| e/e | 29 | 29 | 43 | 39 | 41 | 41 |
| e/h | 52 | 52 | 49 | 48 | 47 | 48 |
| h/h | 51 | 51 | 52 | 54 | 53 | 53 |
| Average effect of an allelic substitution° | 4.6 + 3.8 | 4.9 + 3.8 | 3.5 + 4.0 | 7.0 + 3.9 | 5.5 + 3.9 | 5.7 + 3.9 |

*Significant at 0.05 level.
+See Table 1 for an explanation of genotype symbols.
°Linear regression coefficient and standard error, respectively.

TABLE 6

Estimates for partial regression coefficients using linear and quadratic contrasts among the 3 genotypic classes at 4 RFLP to predict colorimetric absorbance value (2TD) (experiment 2).

| Variable* | Parameter estimates | |
|---|---|---|
| | Coefficient | Std. error |
| Constant | 241.8 | 61.2 |
| L-C22 | 63.6 | 75.8 |
| L-D81 | 165.0 | 75.4 |
| L-I28 | 132.0 | 66.8 |
| Q-C56 | −52.9 | 28.9 |
| L-C22 × L-D81 | 277.1 | 110.9 |

TABLE 6-continued

Estimates for partial regression coefficients using linear and quadratic contrasts among the 3 genotypic classes at 4 RFLP to predict colorimetric absorbance value (2TD) (experiment 2).

| Variable* | Parameter estimates | |
|---|---|---|
| | Coefficient | Std. error |
| L-C22 × L-D81 × L-I28 | 220.6 | 123.0 |

*L and Q indicate the linear and quadratic contrasts among the 3 genotypic classes at each RFLP, respectively.

EXAMPLE II

The overall objective of this experimental on water-use efficiency was the development of more water-use efficient crop cultivars, i.e., in spite of being more conservative water users. Water-use efficient cultivars would result in reduced cost and volume of supplemental irrigation, in the reclamation of marginal land for farming purposes, and in minimization of the rate and extent of man-made soil salinization.

Measurement of the relative water-use efficiency of an array of many hundreds of breeding lines requires expensive specialized equipment and many man hours of labor. Currently, the most precise measurement of the season long water-use efficiency of a specific plant genotype is through determination of the relative abundance of stable carbon isotopes of plant tissue samples. The ratio of stable carbon isotopes has been shown to correlate well with stomatal behavior and the water-use efficiency of the plant. The computed parameter is the ratio of isotopes of Carbon 13 to Carbon 12 in the plant tissue. Although the measurement of stable carbon isotopes is a very accurate measure of the water-use efficiency of a plant, determination of relative abundance of carbon isotopes is expensive.

Therefore, the specific objective of this research was to identify RFLPs associated with the ratio of Carbon 13 to Carbon 12 and, hence, to water-use efficiency of the plant. Identification of associated RFLPs will permit more efficient selection of water-use efficient genotypes by permitting evaluation of seedlings grown in the greenhouse at any time during the year, rather than having to grow the genotypes to maturity in water deficient environments in the field.

A wild species of tomato from the arid regions of Peru, *Solanum pennellii*, has been reported to be tolerant of drought conditions (Rick 1982). $F_1$ hybrids were obtained between *S. pennellii* and UC82, a cultivar of the domesticated tomato *Lycopersicon esculentum*. The $F_1$ hybrid was self-pollinated to produce a segregating $F_2$ population. Seeds were harvested from individual $F_2$ plants to produce $F_3$ families. Over 100 $F_3$ families were grown in a replicated trial in Visalia, Calif. under optimum water availability. The $F_3$ families were also grown in a replicated trial at the same time and location at ⅓ of optimum water availability, i.e., in a water deficient environment. Leaf tissue samples were harvested from each of the $F_3$ families grown in the water deficient environment, and the water-use efficiency determined from the ratio of stable carbon isotopes. The $F_3$ families were ranked from high to low based on their water-use efficiency, and the ten highest and ten lowest families were selected for RFLP analysis. Remanent $F_3$ seed of the 20 selected families was sown in the greenhouse and, when sufficient growth had occurred, leaf tissue was harvested and the DNA extracted for RFLP analysis. The procedures for DNA extraction and Southern blotting were identical to those used in the experiments outlined above.

Seventeen random RFLPs located on 14 different linkage groups were screened for association with expression of water-use efficiency (FIG. 6). Three RFLPs located on 3 different linkage groups, B85, F4 and Q90 were found to be associated with expression of water-use efficiency (Table 7). The linear contrasts among genotype means were significant for all 3 RFLPs, and in addition, the quadratic contrast was significant for RFLP Q90. This suggests that although the predominant type of gene action involved in the expression of water-use efficiency was additive, some dominant gene action was associated with one RFLP.

Figure 7:
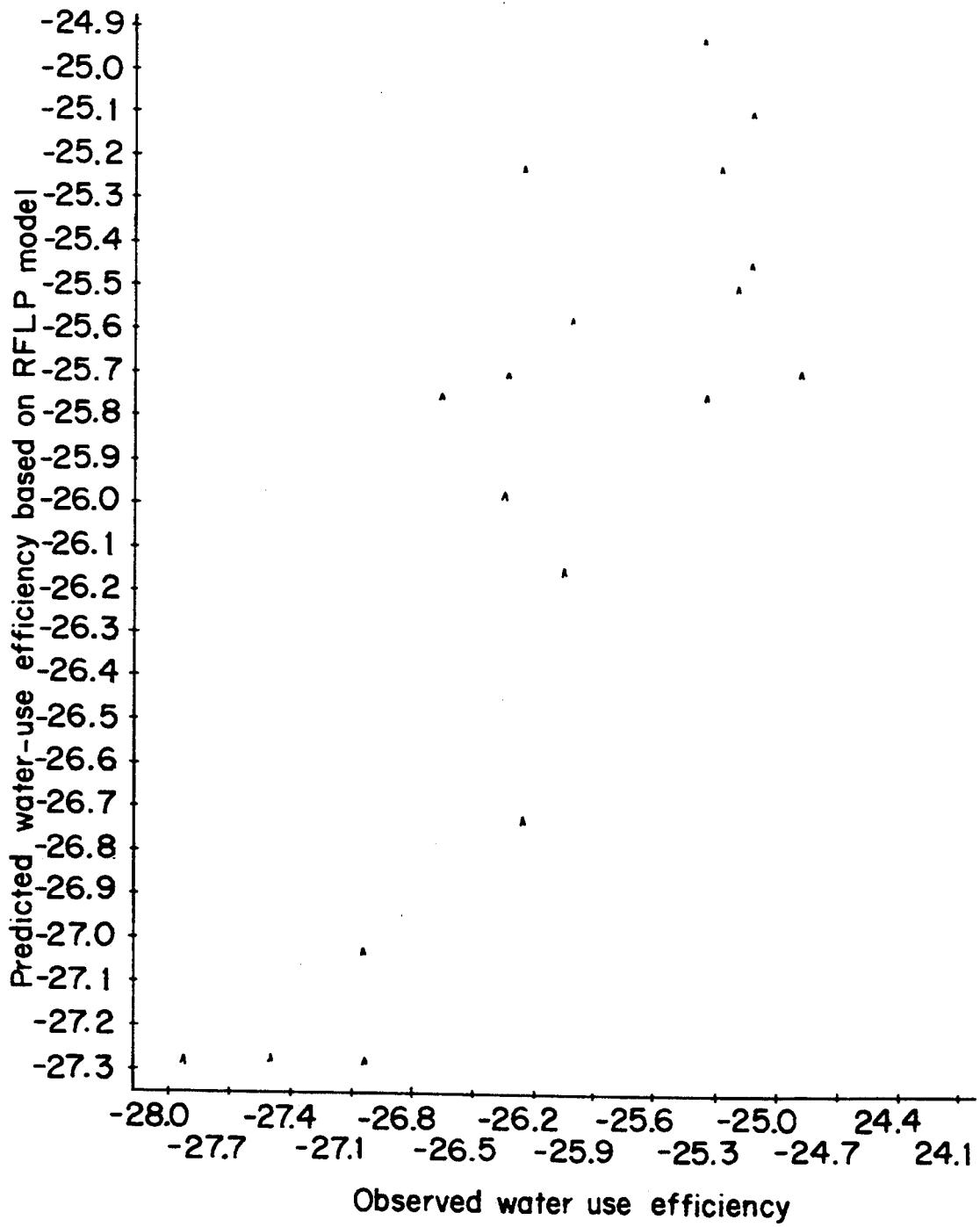
FIG. 7 shows the correlation between observed water-use efficiency versus predicted water-use efficiency based on a multiple regression model.

A multiple regression model was developed which included main effects for the linear contrast at 3 RFLP plus the quadratic effect for RFLP Q90 (Table 8). The multiple regression model accounted for 70% of the observed phenotypic variance for water-use efficiency (FIG. 7). The magnitude of the correlation between observed vs. predicted water-use efficiency suggests that indirect selection for genotypes at 3 RFLP should be effective in selection for improved water-use efficient cultivars.

Figure 8:
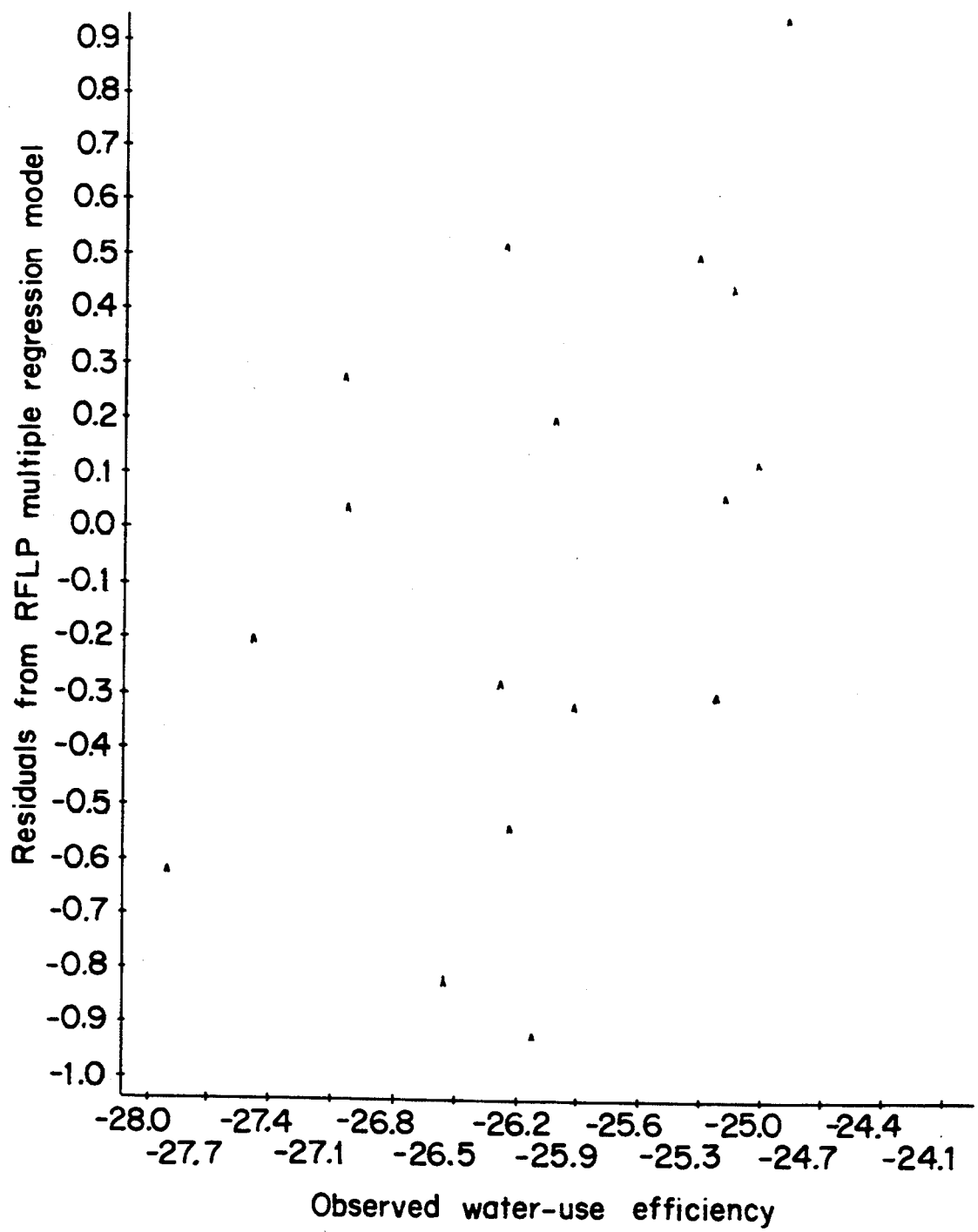
FIG. 8 is a plot of observed water-use efficiency versus residuals from a multiple regression model.

No systematic deviation from randomness was observed in the plot of residuals from the multiple regression model vs. observed water-use efficiency (FIG. 8). This suggests that, although only 17 RFLPs were screened, the major RFLPs associated with expression of water-use efficiency were identified.

TABLE 7

Analysis of variance, linear and quadratic contracts, genotype means and linear regression coefficients for 3 RFLPs associated with expression of water-use efficiency.

| Source | d.f. | B85 | F04 | Q90 |
|---|---|---|---|---|
| Genotype | 2 | | | |
| linear | 1 | 2.912* | 3.929* | 4.252** |
| quadratic | 1 | 0.723 | 0.006 | 3.193* |
| Error | 18 | 0.650 | 0.721 | 0.397 |
| Genotype | | means | | |
| e/e | | −25.36 | −25.31 | −25.61 |
| e/p | | −25.49 | −25.83 | −25.51 |
| p/p | | −26.49 | −26.44 | −27.11 |
| Linear regression coefficient ± Std. error | | 0.66 ± .25 | 0.57 ± .23 | 0.88 ± .27 |
| $r^2$ | | 0.28 | 0.26 | 0.39 |

TABLE 8

Multiple regression model, using genotypic values at 3 RFLPs to predict water-use efficiency.

| | Parameter | Estimate | Std. Error |
|---|---|---|---|
| | intercept | −25.936 | .163 |
| linear | B85 | 0.292 | .222 |
| linear | F04 | 0.241 | .187 |
| linear | Q90 | 0.555 | .241 |
| quadratic | Q90 | −.241 | .097 |
| $r^2 = 0.702$ | | | |

EXAMPLE III

Among the traits in tomato which are of greatest importance to the processing industry is the soluble solids (SS) content of the fruit, which includes fructose, glucose and other sugars. Tomatoes used in formulating solids-based products are often priced according to their SS content and, because of the large amount of tomatoes grown worldwide for processing, small increases in the SS content of the raw tomatoes can have an enormous economic impact. Although the cultivated tomato (*Lycopersicon esculentum*) is relatively low in SS (approximately 5%), some wild relatives of the tomato have much higher proportions. One accession, LA 1028, of a wild relative (*L. chmielewskii*) has an SS content of approximately 10%. The heritability of SS is relatively low in adapted populations and, in addition, expression of SS in tomato fruit is known to be affected by both environment as well as genotype by environment interaction effects. Hence, the heritability of SS is low.

The objective of this experiment was the identification of RFLP genetic markers linked to a gene or genes conferring high SS in tomato fruit. Such information will be very useful in facilitating the development of tomato cultivars with higher levels of SS compared to currently grown varieties.

$F_1$ Hybrids were produced from a cross between *L. chmielewskii* accession LA 1028 and UC82, a widely grown processing tomato cultivar. $F_2$ seeds were harvested from the $F_1$ plants, and grown as individual plants. Fruits were harvested from each of 250 individual $F_2$ plants and the seed extracted. These seeds represented $F_3$ families corresponding to each individual $F_2$ plant. One hundred $F_3$ families were grown in a replicated trial in Visalia Calif. Each plot included 30 plants spaced 6 inches apart and each family was replicated 3 times in a 10×10 triple lattice experimental design.

SS content of fruit were evaluated at 3 times: (1) approximately 10 days before the check cultivar UC82 was fully mature, (2) at full maturity of UC82, and (3) 10 days after UC82 was fully mature. At each SS evaluation 25 fruit were harvested from each plot. The fruit were ground in a blender and the percentage SS in the filtered juice was measured as degrees Brix on a refractometer.

Figure 9:
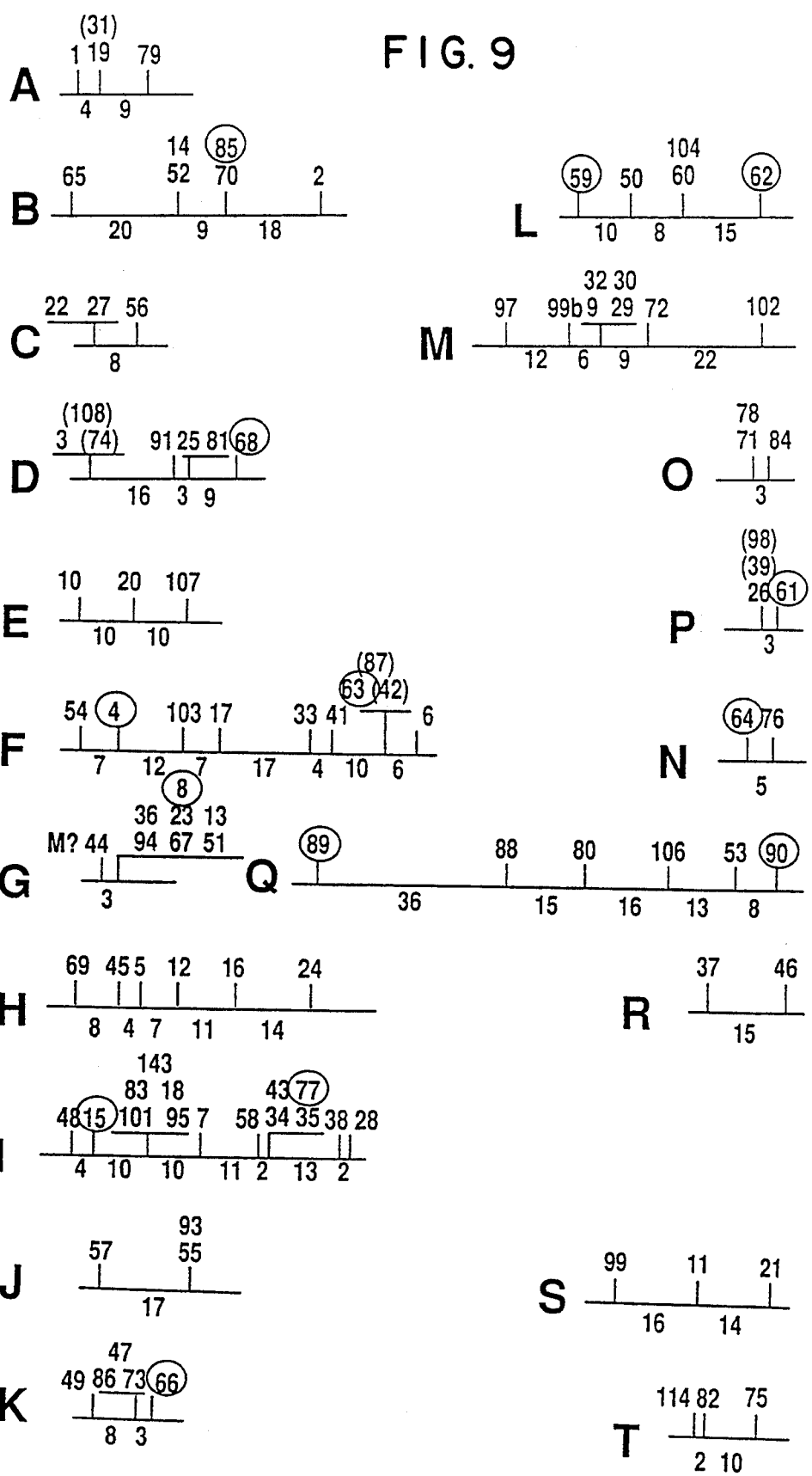
FIG. 9 shows RFLP loci that were found to be associated with the expression of soluble solids (circled).

Leaf tissue samples were harvested from each $F_3$ family grown in the field, and DNA extracted for RFLP analysis using the same procedures used in previous experiments. Ninety nine (99) RFLPs were screened for association with the expression of SS. Of the 99 RFLPs screened, 7 loci on 7 different linkage groups were found to be associated with the expression of SS (FIG. 9).

Analysis of variance was computed for the 7 RFLPs associated with expression of SS, and the 3 genotypic classes at each RFLP (i.e., e/e, e/c and c/c) were partitioned into linear and quadratic contrasts (Table 9). Both the linear and quadratic contrasts were significant for RFLPs T031, T096, T090 and T020. For all 4 RFLPs however, the linear contrast was consistently larger than the quadratic. Only the linear contrasts were significant for RFLPs T069 and T009. In contrast, only the quadratic contrast was significant for RFLP T050. The results would suggest that, although additive gene action was predominant in the expression of SS for most RFLP non-additive (dominant) type gene action was also of some importance.

The 7 RFLPs were fit in a stepwise multiple regression model to select the most predictive RFLP (Table 10). The final prediction model included linear and quadratic main effects for individual RFLPs as well as first-order (epistatic) interaction effects for pairs of RFLPs. The coefficient of determination ($r^2$), i.e., the amount of phenotypic variance for SS which could be accounted for by the multiple regression model, was 56% (Table 10).

Figure 10:
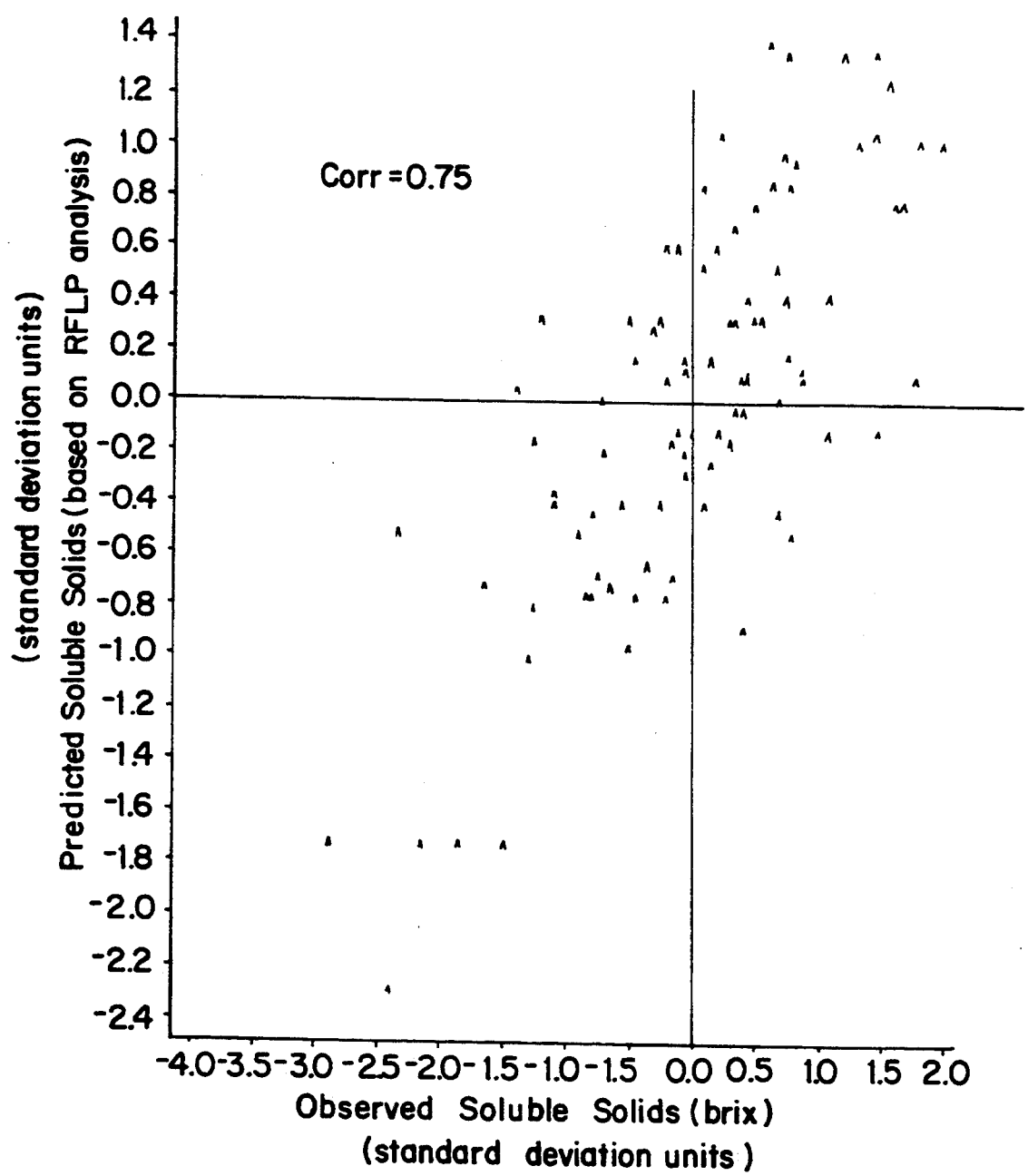
FIG. 10 displays the correlation between observed versus expected expression of soluble solids.
Figure 11:
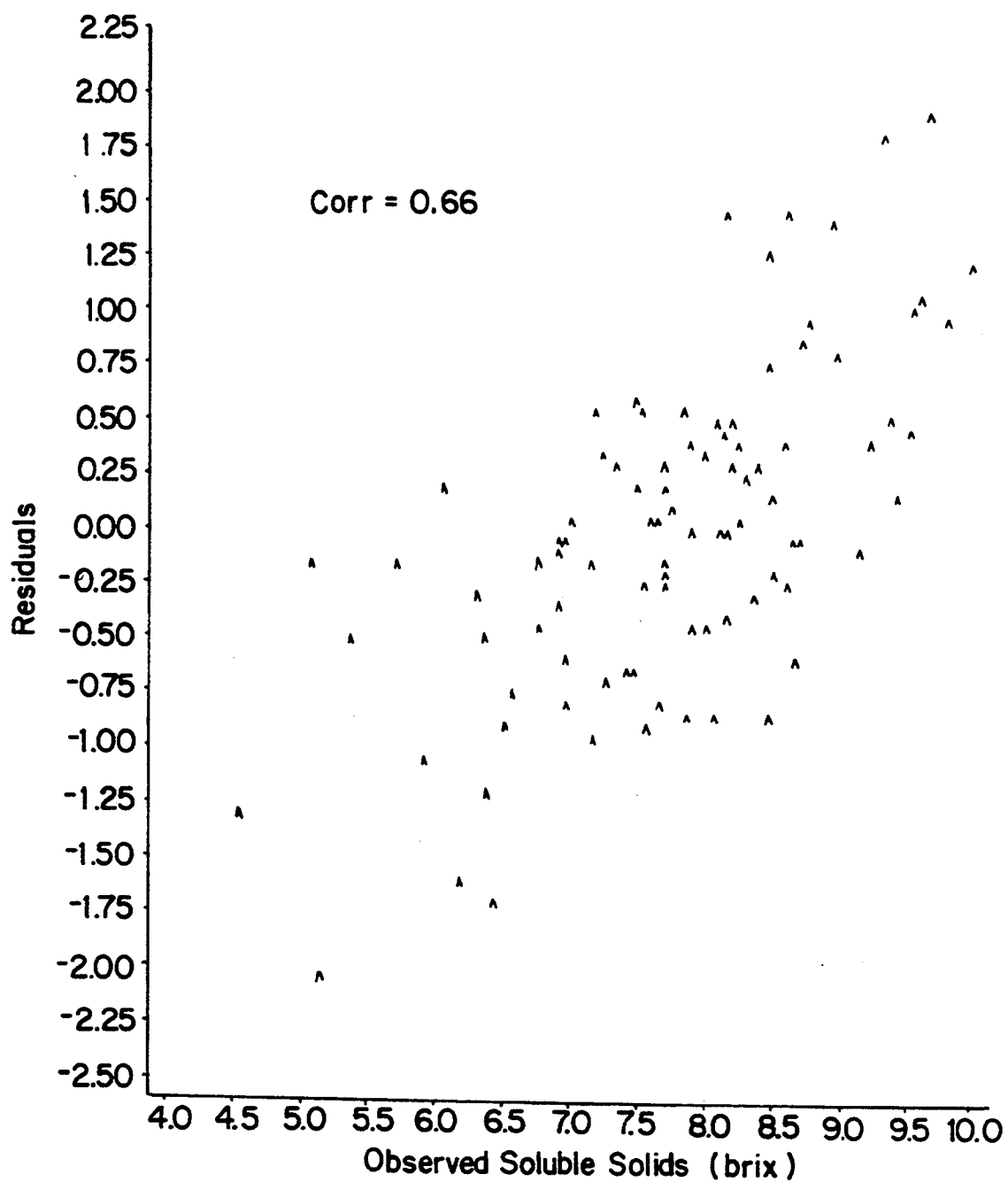
FIG. 11 is a plot of residuals from a regression model versus observed soluble solids.

The correlation between observed and expected expression of SS based on the RFLP regression model was 0.75 (FIG. 10). The magnitude of the correlation suggests that genotypes of RFLPs can be used to predict SS of tomato fruit. This result permits the identification of tomato genotypes grown in the greenhouse which would be expected to have higher levels of expression of SS. A systematic deviation from randomness was observed in the plot of residuals (deviations of observed vs. predicted values) against observed SS (FIG. 11). The pattern of residuals would suggest that one or more additional RFLPs which were not identified in this study may be important in the expression of SS.

TABLE 9

Analysis of variance, linear and quadratic contrasts, genotype means, and linear regression coefficient for 7 RFLPs associated with the expression of soluble solids in tomato fruit.

| Source | d.f. | T031 | T096 | T090 | T050 | T069 |
|---|---|---|---|---|---|---|
| Rep | 2 | 1.08 | 1.10 | 1.02 | 1.12 | 0.90 |
| Genotype | 2 | — | — | — | — | — |
| Linear | 1 | 18.272** | 18.932** | 5.00** | 4.29 | 25.82** |
| Quadratic | 1 | 6.45* | 9.004* | 3.39* | 17.44** | 1.97 |
| Rep × Genotype | 4 | 0.44 | 0.98 | 0.32 | 1.06 | 0.76 |
| Pool W/I Genotype | 291 | 1.59 | 1.70 | 1.75 | 1.67 | 1.68 |
| e/e | | 7.25 | 7.92 | 7.56 | 7.45 | 7.27 |
| e/c | | 8.09 | 7.93 | 7.98 | 8.15 | 7.95 |
| c/c | | 8.23 | 7.19 | 7.94 | 7.81 | 8.27 |
| Linear Regression Coefficient + Std. Error | | 0.64 ± .18 | −0.29 ± .15 | 0.24 ± .16 | 0.30 ± .16 | 0.58 ± .17 |

TABLE 10

Multiple regression coefficients using 5 RFLPs to predict the level of soluble solids in tomato fruit.

| Parameter | Coefficient | Std. Error |
|---|---|---|
| Intercept | 7.83 | 0.10 |
| Linear T020 | 0.51 | 0.13 |
| Linear T031 | 0.43 | 0.15 |
| Linear T096 | −0.48 | 0.11 |
| Linear T050 | 0.12 | 0.12 |
| Linear T069 | 0.28 | 0.14 |
| Quadratic T050 | 0.12 | 0.06 |
| Quadratic T020 | 0.22 | 0.06 |
| Linear T031 × Linear T069 | −0.50 | 0.22 |
| Quadratic T020 × Quadratic T069 | −0.09 | 0.03 |
| Linear T096 × Quadratic T050 | 0.15 | 0.07 |
| $r^2 = 0.56$ | | |

EXAMPLE IV

Among the traits in tomato which are of interest to the processing industry is the size (weight) of tomato fruit. Tomato fruit which are too small cannot be efficiently harvested with mechanized tomato harvesting equipment. In contrast, tomatoes which are too large are subject to greater damage from crushing in transport from the field to the processing plant.

The cultivated tomato *Lycopersicon esculentum* is relatively low in tomato fruit weight (approx. 5%), although some wild relatives of the tomato have much higher fruit weight proportions. One accession, LA 1028, of a wild relative, *L. chmielewskii*, has a tomato fruit weight content of approximately 10%. We have used RFLP technology and crosses involving *L. chmielewskii* to increase the soluble solids content of tomato fruit, as noted above. Because the *L. chmielewskii* tomato fruit are quite small, about 2 cm in diameter, we were also interested in improved fruit size.

The objective of this experimental study was the identification of RFLP genetic markers linked to a gene or genes associated with the expression of tomato fruit weight. Such information will prove very useful in facilitating the development of tomato cultivars which combine higher levels of tomato fruit weight with adequate fruit size.

$F_1$ hybrids were produced from a cross between *L. chmielewskii* accession LA 1028 and UC82, a widely grown processing tomato cultivar. $F_2$ seeds were harvested from the $F_1$ plants, grown as individual plants, and the seed extracted. These seeds represented $F_3$ families corresponding to each individual $F_2$ plant. One hundred $F_3$ families were grown in a replicated trial in Visalia, Calif. Each plot included 30 plants spaced 6 inches apart and each family was replicated 3 times in a $10 \times 10$ triple lattice experimental design.

Fruit weight was evaluated at 3 times: (1) approximately 10 days before the check cultivar UC82 was fully mature, (2) at full maturity of UC82, and (3) 10 days after UC82 was fully mature. At each occasion, 25 fruit were harvested from each plot and total fruit weight determined. Average fruit weight was calculated as total fruit weight divided by the number of fruit harvested from each plot.

Figure 12:
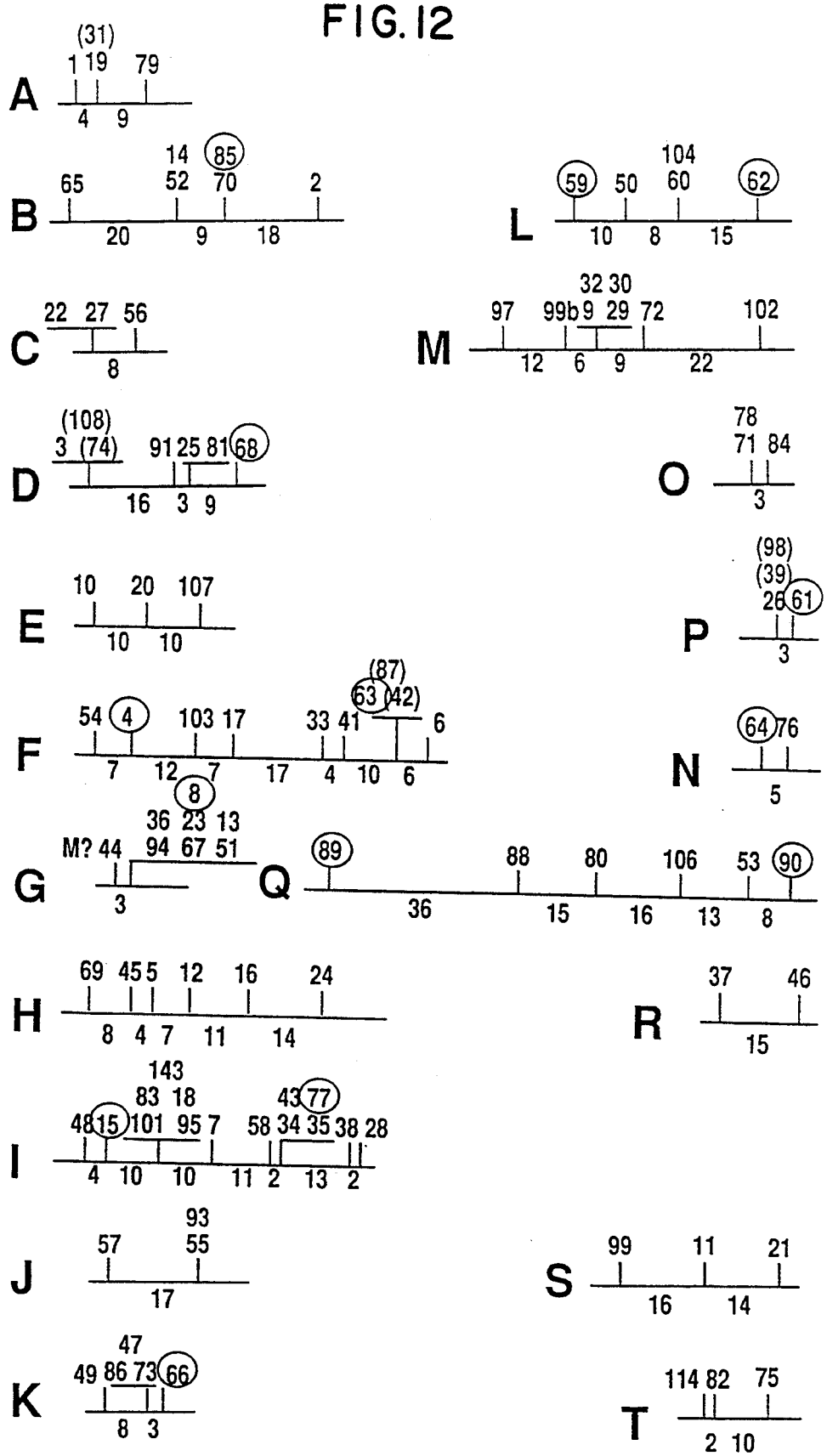
FIG. 12 shows RFLP loci that were found to be associated with the expression of tomato fruit weight (circled).

Leaf tissue samples were harvested from each $F_3$ family grown in the field and DNA was extracted for RFLP analysis by the same procedure used in the above Examples. Ninety nine (99) RFLPs were screened for association with the expression of tomato fruit weight. Of the 99 RFLPs screened, 6 RFLPs on 6 different linkage groups were found to be associated with the expression of tomato fruit weight (FIG. 12).

Analysis of variance was computed for the 6 RFLPs associated with expression of tomato fruit weight and the 3 genotypic classes at each RFLP (i.e., e/e, e/c and c/c) were partitioned into linear and quadratic contrasts (Table 11). Both the linear and quadratic contrasts were significant for all RFLPs. The linear contrast was consistently larger than the quadratic, except for RFLP T009, in which the quadratic contrast was larger. The results suggest that although additive gene action was predominant in the expression of tomato fruit weight for most RFLPs non-additive (dominant) type gene action was also of some importance.

The 6 RFLPs were fit in a stepwise multiple regression model to select the most predictive RFLPs (Table 12). The final prediction model included linear and quadratic main effects for individual RFLPs as well as first-order (epistatic) interaction effects for pairs of RFLPs, and a complex interaction term involving 5 RFLPs. The coefficient of determination ($r^2$), i.e., the amount of phenotypic variance for tomato fruit weight which could be accounted for by the multiple regression model was 59% (Table 12).

Figure 13:
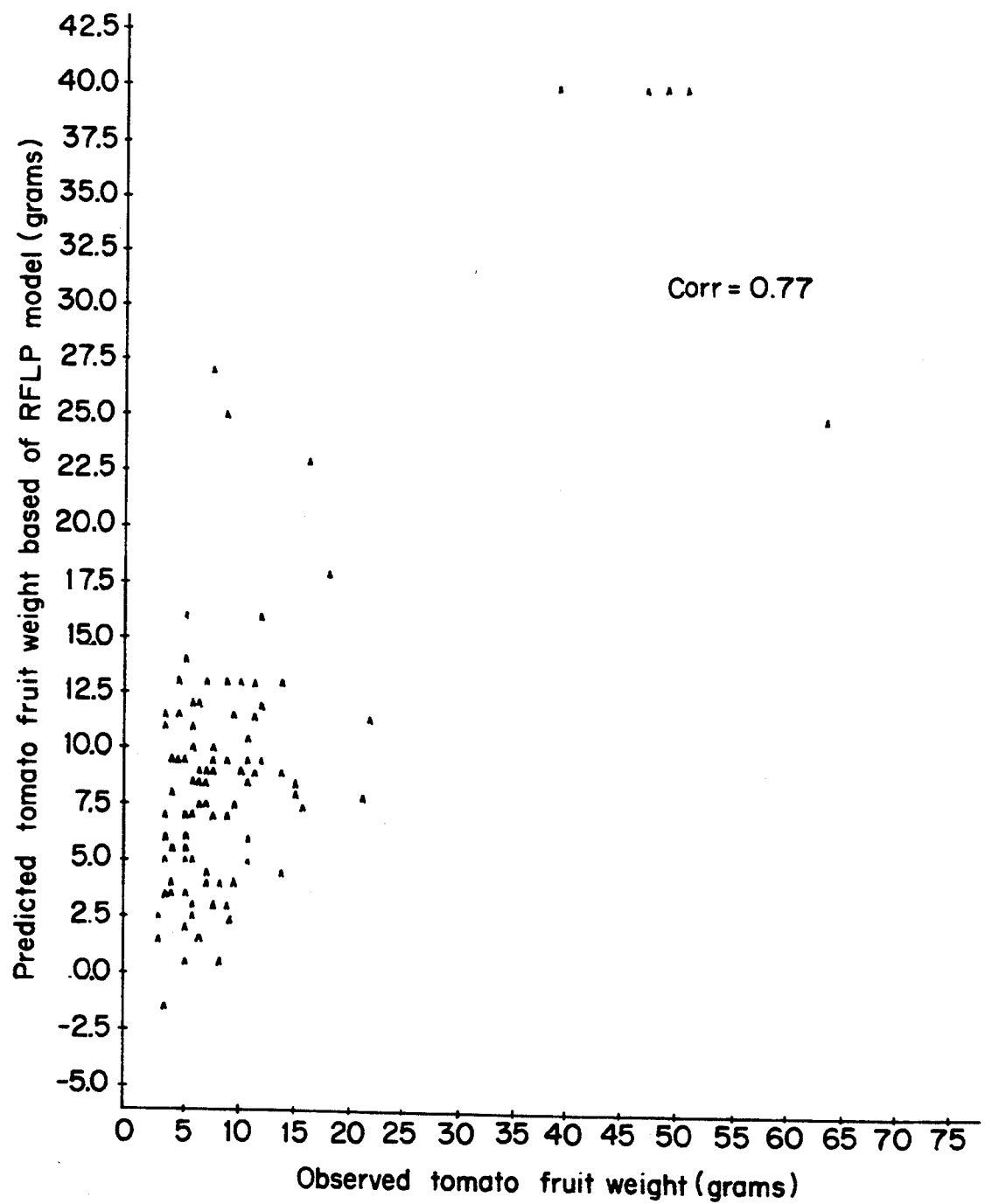
FIG. 13 illustrates the correlation between observed versus expected expression of tomato fruit weight.

The correlation between observed and expected expression of tomato fruit weight (based on RFLP regression model) was 0.77 (FIG. 13). The magnitude of the correlation demonstrates that genotypes of RFLPs can be used to predict weight of tomato fruit. This result permits the identification of tomato genotypes grown in the greenhouse which would be expected to have higher levels of expression of tomato fruit weight.

Figure 14:
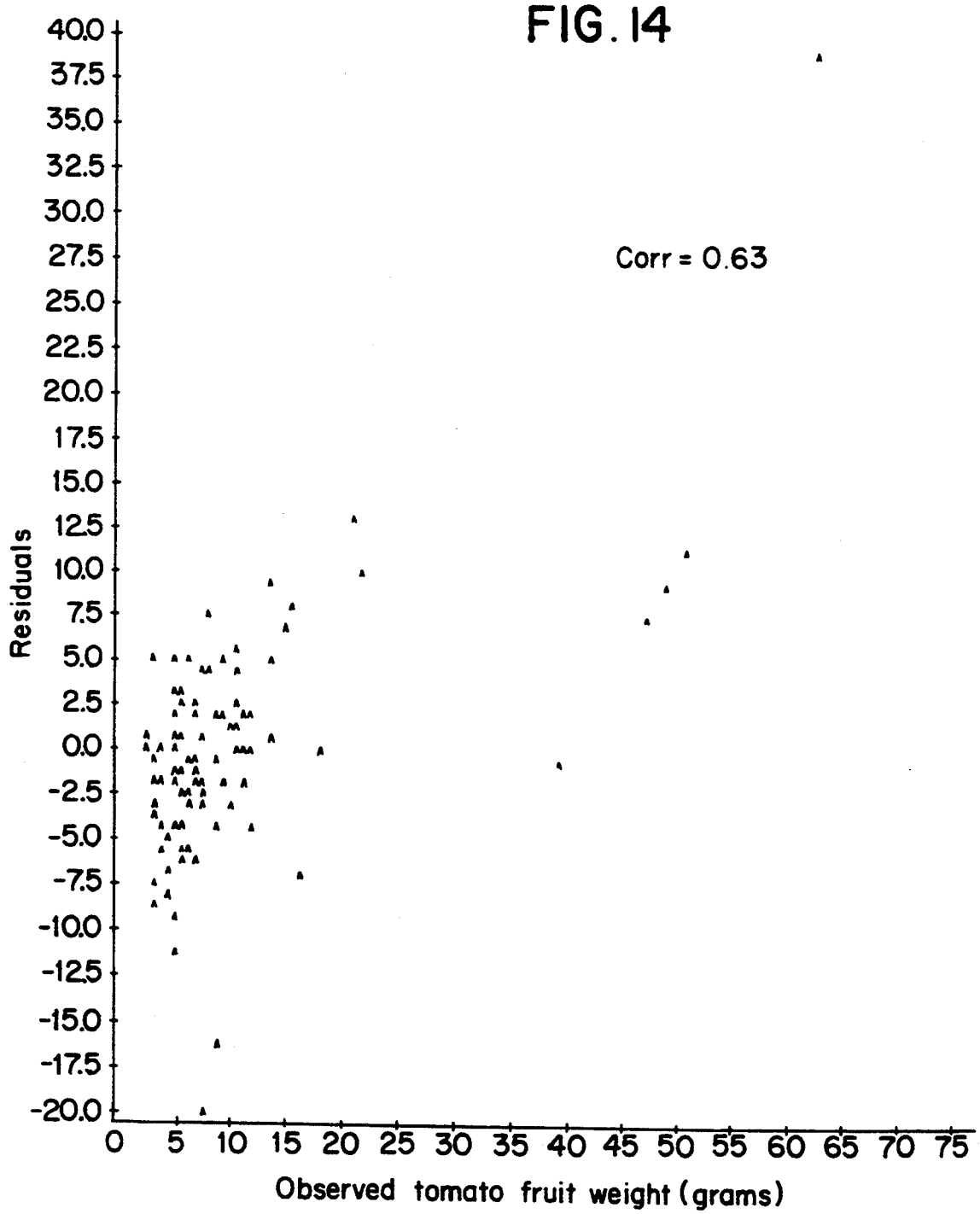
FIG. 14 shows the correlation between residuals from a regression model versus observed values of tomato fruit weight.

A systematic deviation from randomness was observed in the plot of residuals (deviations of observed vs. predicted values) vs. observed tomato fruit weight. The correlation between residuals and observed values was 63% (FIG. 14). The magnitude of this correlation suggests that one or more additional RFLPs which were not identified in this study, may be important in the expression of tomato fruit weight.

TABLE 11

Analysis of variance, linear and quandratic contrasts, genotype means, and linear regression coefficients for 6 RFLPs associated with expression of fruit weight.

| Source | d.f | T020 | T009 | T069 | T090 | T099 | T096 |
|---|---|---|---|---|---|---|---|
| Rep | 2 | 58.50 | 51.3 | 56.4 | 59.8 | 66.2 | 58.6 |
| Genotype | 2 | — | — | — | — | — | — |
| linear | 1 | 6164.0** | 316.3** | 1561.0** | 2547.9** | 909.6** | 1317.5** |
| quadratic | 1 | 1182.3** | 696.0** | 493.3** | 197.2** | 400.6** | 567.6 |
| Rep & Genotype | 4 | 8.68 | 18.9 | 15.8 | 11.9 | 24.44 | 15.0 |
| W/I genotype error | 282 | 114.5 | 119.5 | 134.0 | 129.7 | 133.1 | 132.8 |
| MEANS (grams) | | | | | | | |
| e/e | | 18.85 | 9.79 | 15.17 | 14.13 | 12.39 | 13.74 |
| e/c | | 8.07 | 8.15 | 8.53 | 8.08 | 6.83 | 7.77 |
| c/c | | 5.38 | 12.79 | 7.50 | 5.54 | 7.07 | 7.69 |
| linear regression coefficient ± | | −6.92 ±1.50 | 1.64 ±1.48 | −4.39 ±1.75 | −4.56 ±1.50 | −3.33 ±1.53 | −3.57 ±1.52 |

TABLE 12

Multiple regression coefficients using 6 RFLPs to predict tomato fruit weight.

| Parameter | Coefficient | Std. Error |
|---|---|---|
| Intercept | 6.75 | 1.07 |
| T020 | 0.75 | 1.59 |
| D009 | 0.76 | 0.51 |
| T069 | −1.50 | 1.31 |
| T090 | −2.39 | 1.22 |
| T099 | −1.67 | 1.08 |
| T096 | −0.12 | 1.12 |
| T020 × T069 | 2.94 | 1.77 |
| T020 × T090 | 5.04 | 1.96 |
| T020 × T099 | 2.78 | 1.64 |
| T020 × T096 | 4.69 | 1.56 |
| T090 × T096 | 3.64 | 1.63 |
| T020 × T069 × T090 × T099 × T096 | −8.33 | 3.12 |

TABLE 12-continued

Multiple regression coefficients using 6 RFLPs to predict tomato fruit weight.

| Parameter | Coefficient | Std. Error |
|---|---|---|
| $r^2 = .59$ | | |

EXAMPLE V

In previous Examples, we have demonstrated the ability of RFLP analysis to improve selection for quantitatively inherited traits. The objective of this experiment was to develop RFLP analysis to facilitate simultaneous selection for multiple traits. The specific objective was to develop a RFLP selection index to permit simultaneous increases in soluble solids (SS) and fruit weight (FW) in tomato.

As noted, the cultivated tomato (*Lycopersicon esculentum*), is relatively low in SS (approx. 5%), although some wild relatives of the tomato have much higher proportions. One accession, LA 1028, of a wild relative, *L. chmielewskii*, has a tomato SS content of approximately 10%. We used crosses involving *L. chmielewskii* to increase the soluble solids content of tomato fruit, but, because the *L. chmielewskii* tomato fruit are quite small (about 2 cm in diameter), we were also interested in improved fruit size.

$F_1$ Hybrids were produced from a cross between *L. chmielewskii* accession LA 1028 and UC82, a widely grown processing tomato cultivar, and $F_2$ seeds were harvested from the $F_1$ plants and grown as individual plants. Fruits were harvested from each of 250 individual $F_2$ plants and the seed extracted. These seeds represented $F_3$ families corresponding to each individual $F_2$ plant. One hundred $F_3$ families were grown in a replicated trial in Visiala, Calif. and Malloa, Chile. Each plot included 30 plants spaced 6 inches apart and each family was replicated 3 times in a 10×10 triple lattice experimental design.

Fruit Weight (FW) and soluble solids (SS) content of the tomato was evaluated at 3 times: (1) approximately 10 days before the check cultivar UC82 was fully mature, (2) at full maturity of UC82, and (3) 10 days after UC82 was fully mature. At each occasion 25 fruit were harvested from each plot and total FW determined. Average fruit weight was calculated as total fruit weight divided by the number of fruit harvested from each plot. The fruit were ground in a blender and the percentage SS in the filtered juice was measured as degrees Brix on a refractometer.

Figure 15:
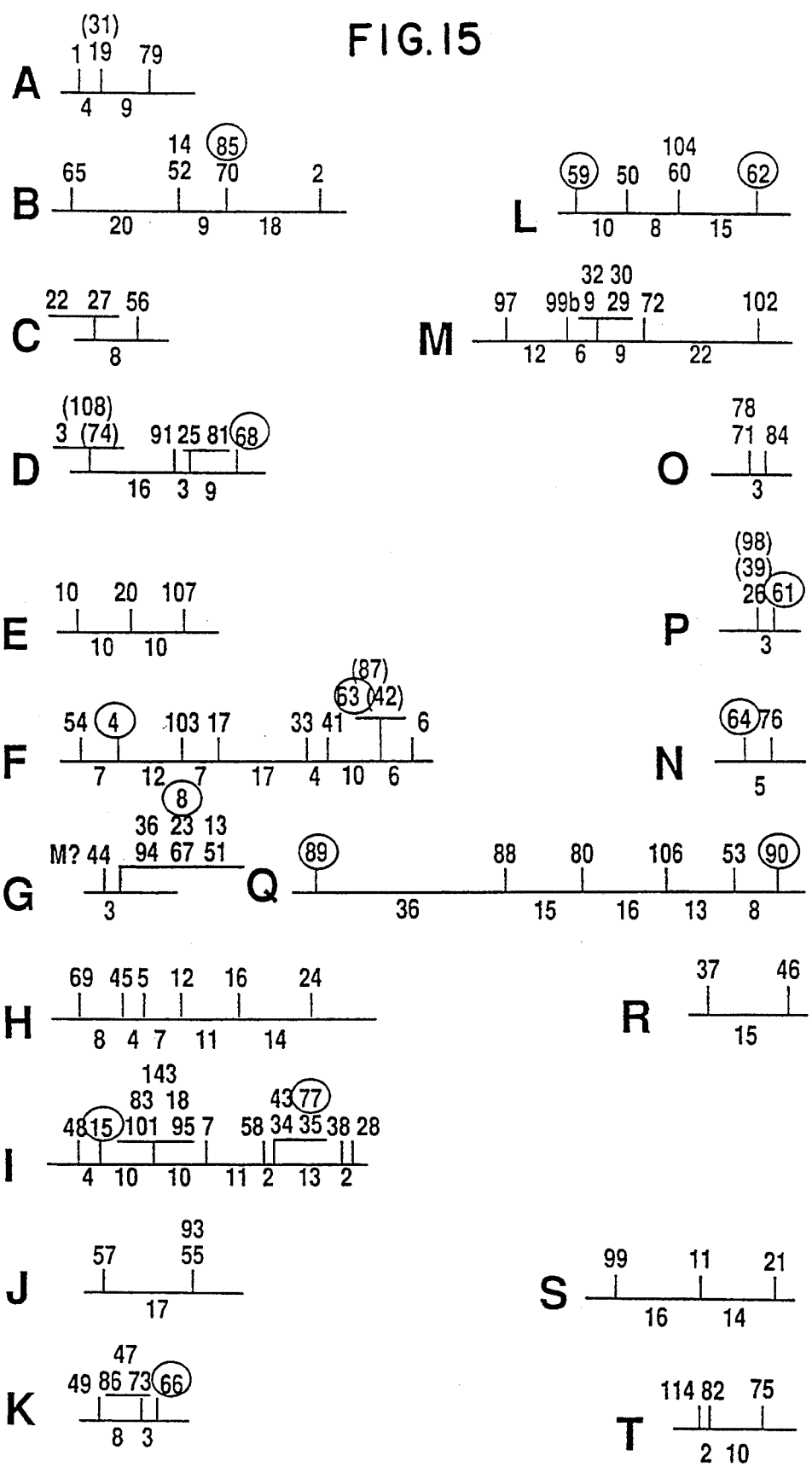
FIG. 15 is a representation of RFLP loci that were found to be associated with the expression of soluble solids in California and Chile and fruit weight (circled).

Leaf tissue samples were harvested from each F3 family grown in the field and DNA extracted for RFLP analysis using the same procedures used in previous Examples. Ninety nine (99) RFLPs were screened for association with the expression of tomato FW and SS content in California and Chile. Of the 99 RFLPs screened, 7 RFLPs on 7 different linkage groups were found to be associated with the three traits of interest, FW, SS Calif. and SS Chile (FIG. 15).

A matrix (Matrix A) was developed which included the linear regression coefficients (Table 13) for each of the 3 traits for each of the 7 RFLPs. The regression coefficients measure the linear effects of each of the RFLPs on expression of the 3 traits. The regression coefficients were standardized to a distribution with mean equal to 0 and variance equal to 1. The standardization permitted the distribution of the 3 traits to be expressed in units of standard deviations and, thus, direct comparisons could be made among the magnitudes of the regression coefficients for each of the 3 traits. The magnitudes of the standarized regression coefficients for all three traits suggest that each of the RFLPs had pleiotropic effects, i.e., that each RFLP was associated with the expression of more than one plant characteristic.

Two vectors (matrices of only 1 column) were developed to represent the relative economic weights of the 3 traits of interest (Table 14). The economic weights chosen for each trait represent the relative importance and direction of selection for each traits. For example, values of $+1$, 0 and $-.5$ would represent the desire to increase the first trait by one unit, maintain the second trait, and decrease the third trait by one half unit, respectively. In this Example, the vector B1 had unit values assigned to SS Chile and SS Calif and zero for fruit weight. In practical terms, vector B1 represents the desire to increase SS in both Calif. and Chile with no change in FW, i.e., broad adaption for soluble solids in both environments. In contrast, vector B2 had unit values assigned to each of the three traits. This would represent the desire to increase all 3 traits simultaneously, with equal weights.

The products of the matrix multiplication of A *B1 and A *B2 are the regression coefficients weighted by their relative economic values. The products of this multiplication are presented in Matrix C (Table 15).

Ten $F_2$ plants were subjected to RFLP analysis, and their genotypes at 7 RFLPs determined. A matrix (Matrix D) was constructed which contained this information (Table 16). The coded genotypic values for each RFLP were as follows: $-1$=e/e esculentum homoygotes, 0=e/c heterozygotes, and 1=c/c chmielewskii homozygotes.

Multiplication of the RFLP genotypes of each F2 plant, Matrix D, by the weighted regression coefficients, Matrix C, results in relative selection index values for each plant, Matrix E (Table 17). The vector B1 represents the selection value of each plant if we wished to select for SS in Calif. and Chile alone. The values can be ranked for purposes of selection. Thus, in this case, the genotypes most likely to result in increased SS in both Calif. and Chile are 57, 26, 60, 75 and 121, in that order. In contrast vector B2 represents the value of each genotype if the objective were to increase SS and FW in both environments. The ranking of the two vectors is similar, except that the value of genotype 121 and 78 is increased relative to the others.

The development of RFLP selection indices permits simultaneous selection for several quantitatively inherited traits as well as environmental adaption. The index could easily be expanded to include many other traits, as the resources necessary for RFLP determination is the same if one considers one or many traits. In practical terms, the construction of RFLP indices greatly facilitates selection, as the RFLP genotype of a plant can be determined from seedlings grown in the greenhouse in the off-season. RFLP selection indices also offer significant advantages over the "intuitive indices" which are merely subjective evalutions of overall performance.

The "B" vectors could be defined to give relative economic weight to an array of plant characteristics. Alternatively, however, they could be used to weigh the importance of several environments. For example, if large genotype by environment interactions were observed for an array of genotypes over several target environments, the "B" vectors could be constructed either to select genotypes best adapted to a specific environment, or to select genotypes with broad adaptation over a range of environments.

TABLE 13

Matrix A. Matrix of standardized regression coefficients for 7 RFLPs associated with soluble solids measured in California and Chile, plus fruit weight measured in California[2].

| RFLP Locus | Soluble Solids Calif. | Soluble Solids Chile | Fruit Weight |
|---|---|---|---|
| 96 | −.229 | −.056 | −.131 |
| 90 | .221 | .038 | −.292 |
| 31 | .433 | .335 | −.268 |
| 9 | −.245 | −.285 | .251 |
| 50 | .161 | .171 | −.198 |
| 69 | .320 | .278 | −.269 |
| 20 | .434 | .173 | −.474 |

[2]Standardization regression coefficients are coefficients calculated on distribution of soluble solids and fruit weight which are transformed to "standard" distribution with mean = 0 and standard deviation = 1.

TABLE 14

Matrix B. Vector of economic weights.

|  | Vector B1 | Vector B2 |
|---|---|---|
| Soluble Solids California | 1 | 1 |
| Soluble Solids Chile | 1 | 1 |
| Fruit Weight | 0 | 1 |

1 This vector would give equal weight for both solids in Califorma and Chile.
2 This vector would weight solids in California and Chile plus fruit weight.

TABLE 15

Matrix C. Products of Matrix Multiplication of A by B and B. The products of this multiplication are vectors of weighted regression coefficients.

| RFLP Locus | A × B1 | A × B2 |
|---|---|---|
| 96 | −.285 | −.416 |
| 90 | .249 | −.043 |
| 31 | .968 | .500 |
| 9 | −.530 | .279 |
| 50 | .332 | .134 |
| 69 | .598 | .329 |
| 20 | .607 | .133 |

TABLE 16

Matrix D. Genotypes of 10 tomato plants at 7 RFLPs.*

| Plant | 96 | 90 | 31 | 9 | 50 | 69 | 20 |
|---|---|---|---|---|---|---|---|
| 26 | 0 | −1 | 1 | −1 | 1 | 1 | 0 |
| 57 | −1 | 1 | 1 | −1 | 0 | 1 | 1 |
| 60 | −1 | 0 | 1 | −1 | 0 | 0 | 0 |
| 64 | 0 | 0 | −1 | 1 | −1 | 0 | 1 |
| 65 | 1 | 0 | 0 | 0 | 0 | 0 | 0 |
| 68 | 1 | 1 | 0 | 0 | 1 | 0 | −1 |
| 74 | 1 | −1 | 0 | 1 | 0 | 0 | 1 |
| 75 | −1 | 0 | −1 | −1 | 1 | 0 | 0 |
| 78 | −1 | −1 | 1 | 1 | 0 | −1 | −1 |
| 121 | −1 | 0 | 1 | 0 | −1 | −1 | 0 |

*
−1 = e/e, esculentum homozygote
0 = e/e, heterozygote
1-c/c, chmielewskii homozygote

TABLE 17

Matrix E. Relative selection index values for 10 F$_2$ tomato plants.

| Plant | B1 | Rank | B2 | Rank |
|---|---|---|---|---|
| 26 | 1.979 | 2 | 1.285 | 2 |

TABLE 17-continued

Matrix E. Relative selection index values for 10 F$_2$ tomato plants.

| Plant | B1 | Rank | B2 | Rank |
|---|---|---|---|---|
| 57 | 3.037 | 1 | 1.614 | 1 |
| 60 | 1.583 | 3 | 1.195 | 3 |
| 64 | −1.023 | 10 | −0.780 | 10 |
| 65 | −0.285 | 6 | −0.416 | 7 |
| 68 | −0.311 | 7 | −0.458 | 8 |
| 74 | −0.457 | 8 | −0.519 | 9 |
| 75 | 0.379 | 4 | 0.329 | 5 |
| 78 | −0.931 | 9 | 0.218 | 6 |
| 121 | 0.123 | 5 | 0.453 | 4 |

[1]Selection for increased soluble solids in both California and Chile.
[2]Selection for increased soluble solids in both California and Chile and fruit weight.

We claim:
1. A breeding program comprising the steps of:
(a) determining the association between restriction fragment length polymorphisms and relative values of a quantitative trait in plants by hybridizing nucleic acid probes specific for the restriction fragment length polymorphisms to genetic material of the plants, determining the relative values of the quantitative traits, and calculating the degree of association between the restriction fragment length polymorphisms and the quantitative trait;
(b) selecting the restriction fragment length polymorphisms that have the highest degree of association with said quantitative trait relative to the restriction fragment length polymorphisms that have been tested;
(c) developing a mathematical model for partitioning the values of the traits among the selected restriction fragment length polymorphisms into linear or quadratic contrasts, or both;
(d) using said contrasts in a multiple regression analysis to determine the predictive value of the selected restriction fragment length polymorphisms for said relative value of the quantitative trait;
(e) manipulating said relative values of the quantitative trait in plants by selecting plants for breeding based on the predictive values of the restriction fragment length polymorphisms; and
(f) breeding said selected plants.
2. The breeding program of claim 1, wherein the relative value of said quantitative trait exhibits continuous variation.
3. The breeding program of claim 1, wherein the nucleic acid probes used for hybridization are selected from a genetic linkage map to be representative of restriction fragment length polymorphisms on all the linkage groups within the map.
4. The breeding program of claim 3, wherein the genetic linkage map is for a plant of the same species as the plants used in the breeding program.
5. The breeding program of claim 1, wherein said step (d) comprises a multiple regression analysis expressed as follows:

$$y = u + b_2(x_1) + b_2(x_2) \ldots + b_n(x_n)$$

where y is equal to an observed value of said trait, u is equal to the mean value of said trait in the plant line, and $b_1$ to $b_n$ are regression coefficients corresponding to selected restriction fragment length genotypes $x_1$ to $x_n$.
6. The breeding program of claim 5 further comprising the step of modifying said multiple regression analysis to reflect interactions among genetically-linked loci.
7. The breeding program of claim 1, further comprising simultaneous selection for a plurality of traits.

* * * * *